US011039576B2

(12) United States Patent
Shimokawa et al.

(10) Patent No.: US 11,039,576 B2
(45) Date of Patent: Jun. 22, 2021

(54) VASCULAR SAP MEASUREMENT SENSOR AND METHOD OF MANUFACTURING VASCULAR SAP MEASUREMENT SENSOR

(71) Applicant: NATIONAL UNIVERSITY CORPORATION KAGAWA UNIVERSITY, Kagawa (JP)

(72) Inventors: Fusao Shimokawa, Kagawa (JP); Akihito Ono, Kagawa (JP); Hidekuni Takao, Kagawa (JP); Kyohei Terao, Kagawa (JP); Tsuyoshi Kobayashi, Kagawa (JP); Ikuo Kataoka, Kagawa (JP)

(73) Assignee: NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 244 days.

(21) Appl. No.: 16/345,229

(22) PCT Filed: Sep. 29, 2017

(86) PCT No.: PCT/JP2017/035407
§ 371 (c)(1),
(2) Date: Apr. 25, 2019

(87) PCT Pub. No.: WO2018/079186
PCT Pub. Date: May 3, 2018

(65) Prior Publication Data
US 2019/0274259 A1    Sep. 12, 2019

(30) Foreign Application Priority Data
Oct. 27, 2016 (JP) .............................. JP2016-210239

(51) Int. Cl.
*A01G 7/00* (2006.01)
*G01F 1/684* (2006.01)

(52) U.S. Cl.
CPC ............... *A01G 7/00* (2013.01); *G01F 1/684* (2013.01)

(58) Field of Classification Search
CPC .................................. A01G 7/00; G01F 1/684
See application file for complete search history.

(56) References Cited

U.S. PATENT DOCUMENTS 3,864,874 A * 2/1975 Norris ...................... A01G 7/06
47/57.5
5,269,183 A * 12/1993 Van Bavel ................ G01F 1/68
73/204.22

(Continued)

FOREIGN PATENT DOCUMENTS

JP      H06-273434 A    9/1994
JP      2015-145810 A   8/2015

*Primary Examiner* — Francis C Gray

(57) ABSTRACT

To provide a vascular sap measurement sensor in which a flow channel that receives incoming flow of vascular sap is unlikely to be blocked by tissues of a plant. A vascular sap measurement sensor 1 includes: a trapping probe 20 for trapping vascular sap; and a support 10 that supports the trapping probe 20. A trapping flow channel 21 that receives incoming flow of the vascular sap is formed in the trapping probe 20. The trapping flow channel 21 has an inlet opening 24 formed on a side surface of the trapping probe 20. This makes it unlikely that the trapping flow channel 21 will be blocked by tissues of a plant when sticking the trapping probe 20 into the plant.

34 Claims, 23 Drawing Sheets

(56) References Cited

U.S. PATENT DOCUMENTS

| | | | | |
|---|---|---|---|---|
| 8,590,373 | B1* | 11/2013 | Van Bavel | G01F 1/6888 |
| | | | | 73/204.23 |
| 10,398,097 | B1* | 9/2019 | Oldewening | A01G 7/00 |
| 2017/0010296 | A1* | 1/2017 | Shimokawa | G01N 33/0098 |
| 2017/0030751 | A1* | 2/2017 | Liu | G01F 1/6888 |
| 2019/0033109 | A1* | 1/2019 | Lee | A01G 23/10 |
| 2019/0257681 | A1* | 8/2019 | Lee | G01N 33/0098 |

* cited by examiner

VASCULAR SAP MEASUREMENT SENSOR AND METHOD OF MANUFACTURING VASCULAR SAP MEASUREMENT SENSOR

TECHNICAL FIELD

This invention relates to a vascular sap measurement sensor and a method of manufacturing the vascular sap measurement sensor. More specifically, this invention relates to a vascular sap measurement sensor usable for trapping vascular sap in a fine point of a plant such as a distal end of a new branch and measuring the dynamics of the vascular sap, and a method of manufacturing the vascular sap measurement sensor.

BACKGROUND ART

In production of crops, fruit, and the like, a plant should be supplied with water or replenished with nutrients at appropriate times that depend on the growing condition of the plant, from the viewpoint of productivity. Thus, grasping the growing condition of the plant properly without affecting the growing of the plant is considerably important.

An actual situation in many agricultural sites is that the growing condition of a plant is generally grasped according to experience based on the number of days without rain or by intuition, for example. However, managing the growing condition of a plant by a method based on experience, and the like is skillful work that involves much expense in time and effort. Additionally, such management uses indexes as a reference that are determined based on personal experience, for example. Hence, not everyone finds it easy to implement such a method of grasping the growing condition of a plant based on experience, etc.

On the other hand, various techniques have been developed in recent years intended to execute water control or fertilization management of crops or fruit based on biological information about a plant. Among these techniques, there is a notable measuring method using the Granier method. There is also a known method of measuring the flow speed of sap using the heat pulse method (see patent literature 1, for example).

Patent literature 1 discloses a device with three rod-shaped temperature sensors and one rod-shaped heater that can be located in a hole formed in a trunk of a tree with a drill, for example. According to a technique disclosed in patent literature 1, the temperature sensors and the rod-shaped heater of the device are located in a hole formed in a sapwood part of the tree. After passage of a predetermined time, the flow speed of sap flowing in the tree is measured based on a temperature difference between these sensors.

The device of patent literature 1 has originally been developed for measurement of the flow speed of sap flowing in a tree having a relatively large stem diameter, and the rod-shaped sensors used in this device have certain degrees of size. Hence, the device of patent literature 1 is inapplicable to a plant having a small stem diameter of about several millimeters.

Measuring a vascular sap flow rate in a plant directly is important for grasping the growing condition of the plant. In particular, measuring the dynamics of vascular sap in a fine point of a plant having a diameter of about several millimeters such as a distal end of a new branch or a pedicel of the plant existing near a crop or a fruit is considerably important for enhancing the productivity and the quality of crops, fruit, and the like.

The present inventors have devised a plant water dynamics sensor usable for measuring the dynamics (water dynamics) of vascular sap flowing in a fine point of a plant such as a distal end of a new branch or a pedicel (patent literature 2). Patent literature 2 discloses a plant water dynamics sensor with various types of probes formed into dimensions allowing the probes to be stuck into a distal end of a new branch, a pedicel, etc. The water dynamics can be measured using the Granier method by sticking the probes into a fine point of a plant and locating the probes in this fine point.

Patent literature 2 states that the plant water dynamics sensor includes a trapping probe with a flow channel that receives incoming flow of vascular sap in a plant.

PRIOR ART LITERATURE

Patent Literature

Patent Literature 1: Japanese Patent Application Publication No. Hei 6-273434
Patent Literature 2: Japanese Patent Application Publication No. 2015-145810

SUMMARY OF INVENTION

Problem to be Solved by Invention

In the plant water dynamics sensor of patent literature 2, an opening of the flow channel that receives incoming flow of the vascular sap is provided at the tip of the trapping probe. Hence, it is likely that sticking the trapping probe into a plant will cause the blockage of the flow channel due to deformation or breakage of tissues of the plant. The blockage of the flow channel with the tissues of the plant causes a problem that incoming flow of the vascular sap will be inhibited.

The plant water dynamics sensor of patent literature 2 includes an electrical resistance probe with an electrical resistance measurement electrode. The position of a xylem is detected based on a difference in electrical resistance between phloem sap and xylem sap, and a depth of sticking of the probe is adjusted. However, sticking the electrical resistance probe into a plant destroys tissues between a xylem and a phloem to cause mixing of the xylem sap and the phloem sap over the surface of the electrical resistance probe. This causes a problem that a measured electrical resistance value will become larger or smaller than an original value to cause reduction in detection accuracy of the position of the xylem.

The plant water dynamics sensor of patent literature 2 includes a heater-equipped temperature probe and a temperature probe used in the Granier method. Sticking these probes into a plant also destroys tissues between a xylem and a phloem to cause mixing of xylem sap and phloem sap. Mixing of the xylem sap and the phloem sap causes a problem that measurement accuracy of a flow rate will be reduced.

A flow channel may be formed in the trapping probe by a method using a technique called sacrificial layer etching used in MEMS technology, for example. Meanwhile, the trapping probe has dimensions allowing the trapping probe to be stuck into a distal end of a new branch, a pedicel, etc. (from 50 μm to 1 mm in length, 50 to 300 μm in width, and 50 μm in thickness, for example). The sacrificial layer etching has difficulty in forming a flow channel inside the trapping probe of such an elongated shape. In this regard, according to patent literature 2, a groove serving as a flow channel is formed on a glass substrate. Then, a silicon substrate is bonded to the glass substrate to form a ceiling. However, such a process has a problem as it involves a complicated step and causes difficulty in achieving manufacture at low cost.

In view of the foregoing circumstances, this invention is intended to achieve any one or two or more of the following objects (1) to (4):

(1) To provide a vascular sap measurement sensor in which a flow channel that receives incoming flow of vascular sap is unlikely to be blocked by tissues of a plant;

(2) To provide a vascular sap measurement sensor achieving high detection accuracy of the position of a xylem;

(3) To provide a vascular sap measurement sensor achieving precise measurement of the flow rate of vascular sap; and (4) To provide a method of manufacturing a vascular sap measurement sensor allowing formation of a flow channel in a probe through a simple process.

Means of Solving Problem (Vascular Sap Measurement Sensor)

A vascular sap measurement sensor according to a first invention includes: a trapping probe for trapping vascular sap; and a support that supports the trapping probe. A trapping flow channel that receives incoming flow of the vascular sap is formed in the trapping probe. The trapping flow channel has an inlet opening arranged on a side surface of the trapping probe.

The vascular sap measurement sensor according to a second invention is characterized in that, in the first invention, the trapping flow channel has two inlet openings, one of the inlet openings is arranged on one of side surfaces of the trapping probe, and the other inlet opening is formed on the other side surface of the trapping probe.

The vascular sap measurement sensor according to a third invention is characterized in that, in the second invention, the trapping flow channel includes: a first flow channel connecting the two inlet openings and extending in the width direction of the trapping probe; and a second flow channel having one end connected to the first flow channel and extending in the axis direction of the trapping probe. A guide wall is provided in the first flow channel. The guide wall guides the vascular sap having flowed into the first flow channel through the inlet opening to the second flow channel.

The vascular sap measurement sensor according to a fourth invention is characterized in that, in the first invention, the trapping flow channel has one inlet opening, and the inlet opening is formed on one side surface of the trapping probe.

The vascular sap measurement sensor according to a fifth invention is characterized in that, in the first, second, third, or fourth invention, a pH measurement element is provided in the trapping flow channel.

The vascular sap measurement sensor according to a sixth invention is characterized in that, in the first, second, third, fourth, or fifth invention, the vascular sap measurement sensor includes an electrical resistance probe with an electrical resistance measurement electrode, the electrical resistance probe is supported on the support, an electrode flow channel that receives incoming flow of the vascular sap is formed in the electrical resistance probe, the electrode flow channel extends in the width direction of the electrical resistance probe, the electrode flow channel has an opening arranged on a side surface of the electrical resistance probe, and the electrical resistance measurement electrode is provided in the electrode flow channel.

The vascular sap measurement sensor according to a seventh invention is characterized in that, in the sixth invention, the electrical resistance probe includes a plurality of the electrode flow channels, the electrode flow channels are aligned in the axis direction of the electrical resistance probe, and each of the electrode flow channels is provided with the electrical resistance measurement electrode.

The vascular sap measurement sensor according to an eighth invention is characterized in that, in the first, second, third, fourth, fifth, sixth, or seventh invention, the vascular sap measurement sensor includes: a heater-equipped temperature probe with a temperature sensor and a heater; and a temperature probe with a temperature sensor. The heater-equipped temperature probe and the temperature probe are supported on the support.

The vascular sap measurement sensor according to a ninth invention is characterized in that, in the eighth invention, a temperature sensor flow channel that receives incoming flow of the vascular sap is formed in the heater-equipped temperature probe, the temperature sensor flow channel extends in the width direction of the heater-equipped temperature probe, the temperature sensor flow channel has an opening arranged on a side surface of the heater-equipped temperature probe, and the temperature sensor is provided in the temperature sensor flow channel.

The vascular sap measurement sensor according to a tenth invention is characterized in that, in the eighth or ninth invention, a temperature sensor flow channel that receives incoming flow of the vascular sap is formed in the temperature probe, the temperature sensor flow channel extends in the width direction of the temperature probe, the temperature sensor flow channel has an opening arranged on a side surface of the temperature probe, and the temperature sensor is provided in the temperature sensor flow channel.

The vascular sap measurement sensor according to an eleventh invention is characterized in that, in the eighth, ninth, or tenth invention, the support is formed of a stack of an insulating substrate and a semiconductor substrate, the heater-equipped temperature probe and the temperature probe are formed at the semiconductor substrate, and the support has a groove where the semiconductor substrate is removed. The groove is formed between a part of the support supporting the heater-equipped temperature probe and a part of the support supporting the temperature probe.

A vascular sap measurement sensor according to a twelfth invention includes: a heater-equipped temperature probe with a temperature sensor and a heater; a temperature probe with a temperature sensor; and a support that supports the heater-equipped temperature probe and the temperature probe. A temperature sensor flow channel that receives incoming flow of vascular sap is formed in the heater-equipped temperature probe, the temperature sensor flow channel extends in the width direction of the heater-equipped temperature probe, the temperature sensor flow channel has an opening arranged on a side surface of the heater-equipped temperature probe, and the temperature sensor is provided in the temperature sensor flow channel.

The vascular sap measurement sensor according to a thirteenth invention is characterized in that, in the twelfth invention, a temperature sensor flow channel that receives incoming flow of the vascular sap is formed in the temperature probe, the temperature sensor flow channel extends in the width direction of the temperature probe, the temperature sensor flow channel has an opening arranged on a side surface of the temperature probe, and the temperature sensor is provided in the temperature sensor flow channel.

A vascular sap measurement sensor according to a fourteenth invention includes: a heater-equipped temperature probe with a temperature sensor and a heater; a temperature probe with a temperature sensor; and a support that supports the heater-equipped temperature probe and the temperature probe. A temperature sensor flow channel that receives incoming flow of vascular sap is formed in the temperature probe, the temperature sensor flow channel extends in the width direction of the temperature probe, the temperature sensor flow channel has an opening arranged on a side surface of the temperature probe, and the temperature sensor is provided in the temperature sensor flow channel.

The vascular sap measurement sensor according to a fifteenth invention is characterized in that, in the twelfth, thirteenth, or fourteenth invention, the support is formed of a stack of an insulating substrate and a semiconductor substrate, the heater-equipped temperature probe and the temperature probe are formed at the semiconductor substrate, and the support has a groove where the semiconductor substrate is removed. The groove is formed between a part of the support supporting the heater-equipped temperature probe and a part of the support supporting the temperature probe.

The vascular sap measurement sensor according to a sixteenth invention is characterized in that, in the twelfth, thirteenth, fourteenth, or fifteenth invention, the vascular sap measurement sensor includes an electrical resistance probe with an electrical resistance measurement electrode, the electrical resistance probe is supported on the support, an electrode flow channel that receives incoming flow of the vascular sap is formed in the electrical resistance probe, the electrode flow channel extends in the width direction of the electrical resistance probe, the electrode flow channel has an opening arranged on a side surface of the electrical resistance probe, and the electrical resistance measurement electrode is provided in the electrode flow channel.

The vascular sap measurement sensor according to a seventeenth invention is characterized in that, in the sixteenth invention, the electrical resistance probe includes a plurality of the electrode flow channels, the electrode flow channels are aligned in the axis direction of the electrical resistance probe, and each of the electrode flow channels is provided with the electrical resistance measurement electrode.

(Method of Manufacturing Vascular Sap Measurement Sensor)

A method of manufacturing a vascular sap measurement sensor according to an eighteenth invention is a method of manufacturing a vascular sap measurement sensor including a trapping probe with a trapping flow channel that receives incoming flow of vascular sap. The method includes: a side wall forming step of forming side walls of the trapping flow channel on a semiconductor substrate, the trapping flow channel having an inlet opening arranged on a side surface of the trapping probe; and a ceiling forming step of forming a ceiling part of the trapping flow channel by thermally fusion-bonding a sheet-like photoresist to stretch the photoresist across the upper ends of the side walls and removing an unnecessary part of the photoresist.

The method of manufacturing a vascular sap measurement sensor according to a nineteenth invention is characterized in that, in the eighteenth invention, in the side wall forming step, the side walls are formed by thermally fusion-bonding a sheet-like photoresist and removing a part of the photoresist corresponding to the trapping flow channel.

The method of manufacturing a vascular sap measurement sensor according to a twentieth invention is characterized in that, in the eighteenth invention, in the side wall forming step, the side walls are formed by removing a part of the semiconductor substrate corresponding to the trapping flow channel.

The method of manufacturing a vascular sap measurement sensor according to a twenty-first invention is characterized in that, in the eighteenth invention, the method includes a hydrophilization step of giving hydrophilic property to the side walls performed after the side wall forming step.

The method of manufacturing a vascular sap measurement sensor according to a twenty-second invention is characterized in that, in the eighteenth invention, the method includes a hydrophilization step of giving hydrophilic property to an interior of the trapping flow channel performed after the ceiling forming step.

A method of manufacturing a vascular sap measurement sensor according to a twenty-third invention is a method of manufacturing a vascular sap measurement sensor including a heater-equipped temperature probe with a temperature sensor flow channel that receives incoming flow of vascular sap. The method includes: a side wall forming step of forming side walls of the temperature sensor flow channel on a semiconductor substrate, the temperature sensor flow channel having an inlet opening arranged on a side surface of the heater-equipped temperature probe; and a ceiling forming step of forming a ceiling part of the temperature sensor flow channel by thermally fusion-bonding a sheet-like photoresist to stretch the photoresist across the upper ends of the side walls and removing an unnecessary part of the photoresist.

The method of manufacturing a vascular sap measurement sensor according to a twenty-fourth invention is characterized in that, in the twenty-third invention, in the side wall forming step, the side walls are formed by thermally fusion-bonding a sheet-like photoresist and removing a part of the photoresist corresponding to the temperature sensor flow channel.

The method of manufacturing a vascular sap measurement sensor according to a twenty-fifth invention is characterized in that, in the twenty-third invention, in the side wall forming step, the side walls are formed by removing a part of the semiconductor substrate corresponding to the temperature sensor flow channel.

The method of manufacturing a vascular sap measurement sensor according to a twenty-sixth invention is characterized in that, in the twenty-third invention, the method includes a hydrophilization step of giving hydrophilic property to the side walls performed after the side wall forming step.

The method of manufacturing a vascular sap measurement sensor according to a twenty-seventh invention is characterized in that, in the twenty-third invention, the method includes a hydrophilization step of giving hydrophilic property to an interior of the temperature sensor flow channel performed after the ceiling forming step.

A method of manufacturing a vascular sap measurement sensor according to a twenty-eighth invention is a method of manufacturing a vascular sap measurement sensor including a temperature probe with a temperature sensor flow channel that receives incoming flow of vascular sap. The method includes: a side wall forming step of forming side walls of the temperature sensor flow channel on a semiconductor substrate, the temperature sensor flow channel having an inlet opening arranged on a side surface of the temperature probe; and a ceiling forming step of forming a ceiling part of the temperature sensor flow channel by thermally fusion-bonding a sheet-like photoresist to stretch the photoresist across the upper ends of the side walls and removing an unnecessary part of the photoresist.

The method of manufacturing a vascular sap measurement sensor according to a twenty-ninth invention is characterized in that, in the twenty-eighth invention, in the side wall forming step, the side walls are formed by thermally fusion-bonding a sheet-like photoresist and removing a part of the photoresist corresponding to the temperature sensor flow channel.

The method of manufacturing a vascular sap measurement sensor according to a thirtieth invention is characterized in that, in the twenty-eighth invention, in the side wall forming step, the side walls are formed by removing a part of the semiconductor substrate corresponding to the temperature sensor flow channel.

The method of manufacturing a vascular sap measurement sensor according to a thirty-first invention is characterized in that, in the twenty-eighth invention, the method includes a hydrophilization step of giving hydrophilic property to the side walls performed after the side wall forming step.

The method of manufacturing a vascular sap measurement sensor according to a thirty-second invention is characterized in that, in the twenty-eighth invention, the method includes a hydrophilization step of giving hydrophilic property to an interior of the temperature sensor flow channel performed after the ceiling forming step.

Advantageous Effects of Invention (Vascular Sap Measurement Sensor)

According to the first invention, the trapping probe is usable for trapping the vascular sap and for analyzing a nutritive substance in the vascular sap accordingly. Further, the inlet opening of the trapping flow channel is arranged on the side surface of the trapping probe. This makes it unlikely that the trapping flow channel will be blocked by tissues of a plant when sticking the trapping probe into the plant.

According to the second invention, the inlet openings of the trapping flow channel are arranged on the opposite side surfaces of the trapping probe. This allows trapping of the vascular sap from either side of the trapping probe.

According to the third invention, the presence of the guide wall in the first flow channel can make it unlikely that the vascular sap having flowed into the trapping flow channel through one of the inlet openings will flow out through the other inlet opening, thereby allowing efficient trapping of the vascular sap.

According to the fourth invention, arranging the inlet opening of the trapping flow channel on only one side of the trapping probe can make it unlikely that the vascular sap having flowed into the trapping flow channel through the inlet opening will flow out, thereby allowing efficient trapping of the vascular sap.

According to the fifth invention, whether the vascular sap having flowed into the trapping flow channel is phloem sap or xylem sap can be determined based on a pH value measured by the pH measurement element.

According to the sixth invention, the position of a xylem can be detected from an electrical resistance measured by the electrical resistance probe to allow adjustment of a depth of sticking of each probe. Further, the provision of the electrical resistance measurement electrode in the electrode flow channel can suppress mixing of the xylem sap and the phloem sap to achieve high detection accuracy of the position of the xylem.

According to the seventh invention, the electrical resistance measurement electrodes are aligned in the axis direction of the electrical resistance probe. This makes it possible to provide a distribution of electrical resistances in a plant, so that the position of the xylem can be determined precisely.

According to the eighth invention, the flow speed of the vascular sap can be determined from a temperature difference between the respective temperature sensors provided at the heater-equipped temperature probe and the temperature probe, and a flow rate can be determined from the determined flow speed.

According to the ninth invention, the provision of the temperature sensor of the heater-equipped temperature probe in the temperature sensor flow channel can suppress mixing of the xylem sap and the phloem sap to achieve precise measurement of a vascular sap flow rate.

According to the tenth invention, the provision of the temperature sensor of the temperature probe in the temperature sensor flow channel can suppress mixing of the xylem sap and the phloem sap to achieve precise measurement of a vascular sap flow rate.

According to the eleventh invention, the provision of the groove between the heater-equipped temperature probe and the temperature probe makes it unlikely that heat of the heater of the heater-equipped temperature probe will be transmitted via the support to the temperature probe. This makes it possible to determine a vascular sap flow rate with high accuracy.

According to the twelfth invention, the provision of the temperature sensor of the heater-equipped temperature probe in the temperature sensor flow channel can suppress mixing of the xylem sap and the phloem sap to achieve precise measurement of a vascular sap flow rate.

According to the thirteenth invention, the provision of the temperature sensor of the temperature probe in the temperature sensor flow channel can suppress mixing of the xylem sap and the phloem sap to achieve precise measurement of a vascular sap flow rate.

According to the fourteenth invention, the provision of the temperature sensor of the temperature probe in the temperature sensor flow channel can suppress mixing of the xylem sap and the phloem sap to achieve precise measurement of a vascular sap flow rate.

According to the fifteenth invention, the provision of the groove between the heater-equipped temperature probe and the temperature probe makes it unlikely that heat of the heater of the heater-equipped temperature probe will be transmitted via the support to the temperature probe. This makes it possible to determine a vascular sap flow rate with high accuracy.

According to the sixteenth invention, the position of the xylem can be detected from an electrical resistance measured by the electrical resistance probe to allow adjustment of a depth of sticking of each probe. Further, the provision of the electrical resistance measurement electrode in the electrode flow channel can suppress mixing of the xylem sap and the phloem sap to achieve high detection accuracy of the position of the xylem.

According to the seventeenth invention, the electrical resistance measurement electrodes are aligned in the axis direction of the electrical resistance probe. This makes it possible to provide a distribution of electrical resistances in a plant, so that the position of the xylem can be determined precisely.

(Method of Manufacturing Vascular Sap Measurement Sensor)

According to the eighteenth invention, the ceiling part of the trapping flow channel is formed using the sheet-like photoresist. Thus, the trapping flow channel can be formed easily in the trapping probe.

According to the nineteenth invention, the side walls of the trapping flow channel are formed using the photoresist. Thus, the resultant side walls can be vertical to the semiconductor substrate and the cross-sectional area of the trapping flow channel can be increased. This allows the vascular sap to easily flow into the trapping flow channel.

According to the twentieth invention, a bottom part and the side walls of the trapping flow channel are formed integrally by the use of the semiconductor substrate to allow increase in the strength of the trapping probe.

According to the twenty-first invention, hydrophilic property is given to the side walls to allow the vascular sap to flow into the trapping flow channel easily.

According to the twenty-second invention, hydrophilic property is given to the interior of the trapping flow channel to allow the vascular sap to flow into the trapping flow channel easily.

According to the twenty-third invention, the ceiling part of the temperature sensor flow channel is formed using the sheet-like photoresist. Thus, the temperature sensor flow channel can be formed easily in the heater-equipped temperature probe.

According to the twenty-fourth invention, the side walls of the temperature sensor flow channel are formed using the photoresist. Thus, the resultant side walls can be vertical to the semiconductor substrate and the cross-sectional area of the temperature sensor flow channel can be increased. This allows the vascular sap to easily flow into the temperature sensor flow channel.

According to the twenty-fifth invention, a bottom part and the side walls of the temperature sensor flow channel are formed integrally by the use of the semiconductor substrate to allow increase in the strength of the heater-equipped temperature probe.

According to the twenty-sixth invention, hydrophilic property is given to the side walls to allow the vascular sap to flow into the temperature sensor flow channel easily.

According to the twenty-seventh invention, hydrophilic property is given to the interior of the temperature sensor flow channel to allow the vascular sap to flow into the temperature sensor flow channel easily.

According to the twenty-eighth invention, the ceiling part of the temperature sensor flow channel is formed using the sheet-like photoresist. Thus, the temperature sensor flow channel can be formed easily in the temperature probe.

According to the twenty-ninth invention, the side walls of the temperature sensor flow channel are formed using the photoresist. Thus, the resultant side walls can be vertical to the semiconductor substrate and the cross-sectional area of the temperature sensor flow channel can be increased. This allows the vascular sap to easily flow into the temperature sensor flow channel.

According to the thirtieth invention, a bottom part and the side walls of the temperature sensor flow channel are formed integrally by the use of the semiconductor substrate to allow increase in the strength of the temperature probe.

According to the thirty-first invention, hydrophilic property is given to the side walls to allow the vascular sap to flow into the temperature sensor flow channel easily.

According to the thirty-second invention, hydrophilic property is given to the interior of the temperature sensor flow channel to allow the vascular sap to flow into the temperature sensor flow channel easily.

EMBODIMENTS FOR CARRYING OUT INVENTION

Figure 1:
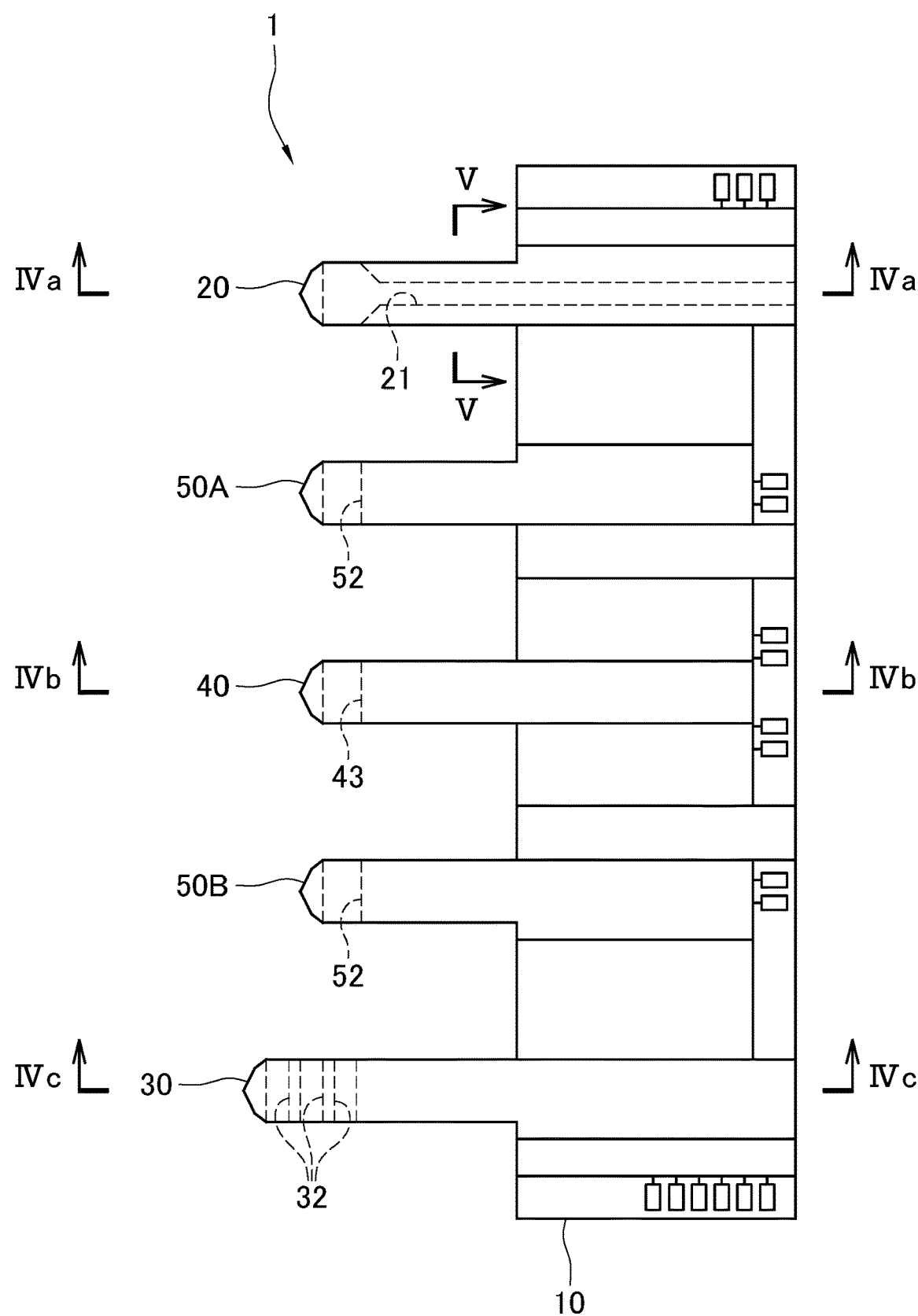
FIG. 1 is a plan view of a vascular sap measurement sensor according to a first embodiment.

Embodiments of this invention are described next based on the drawings.

First Embodiment

A vascular sap measurement sensor 1 according to a first embodiment of this invention can be attached easily to a fine point of a plant such as a distal end of a new branch (hereinafter simply called a new branch distal end) or a pedicel of a plant. The vascular sap measurement sensor 1 has a function of trapping vascular sap in the fine part of the plant and a function of measuring the dynamics of the vascular sap.

(Granier Method)

The vascular sap measurement sensor 1 is used for measuring the dynamics of vascular sap in a plant using the Granier method. Principles of determining the flow speed of sap flowing in a tree and determining a flow rate from the flow speed using the Granier method will be described briefly.

The Granier method is to calculate a sap flow rate F using a Granier sensor. The Granier sensor includes rod-shaped probes in a pair. These probes in a pair each include a temperature sensor. One of the probes in a pair includes a heater. The probe with the temperature sensor and the heater will be called a heater-equipped temperature probe HP. The other probe is a probe used for reference. The probe only including the temperature sensor will be called a temperature probe RP.

A method of installing the Granier sensor on a tree and measuring the sap flow rate F in the tree will be described below.

First, holes are formed in two places of the trunk of the tree with a drill, for example. The heater-equipped temperature probe HP and the temperature probe RP of the Granier sensor are inserted in the corresponding holes to be installed on the tree and left at rest for one day or more. The temperature probe RP and the heater-equipped temperature probe HP of the Granier sensor are aligned in this order along a sap flow in a direction from an upstream side toward a downstream side. More specifically, if sap flows in a direction from a root toward a distal end, the temperature probe RP is inserted in a hole closer to the root and the heater-equipped temperature probe HP is inserted in a hole closer to the distal end.

Next, the heater of the heater-equipped temperature probe HP of the Granier sensor is started. This generates temperature difference ΔT between the respective temperature sensors of the probes HP and RP in a pair. As shown by the following formula 1, the temperature difference ΔT is used as a function of a sap flow speed u. By using this function, the sap flow speed u can be calculated based on the temperature difference ΔT.

$$u = \frac{1}{\alpha}\left\{\frac{\Delta T(0) - \Delta T(u)}{\Delta T(u)}\right\}^{\frac{1}{\beta}} = \frac{1}{\alpha}K^{\frac{1}{\beta}}$$ [Formula 1]

In this formula, u is an average sap flow speed [m/s], ΔT(u) is temperature difference [° C.] between the heater-equipped temperature probe HP and the temperature probe RP determined if an average sap flow speed is u, ΔT(0) is a maximum temperature [° C.] of ΔT, and α and β are coefficients obtained from observed data.

Based on the following formula 2, the sap flow rate F can be calculated using the sap flow speed u.

$$F = u \times S$$ [Formula 2]

In this formula, F is a sap flow rate [m³/s] and S is a cross-sectional area [m²] formed by the probes HP and RP in a peripheral direction of a trunk.

If the flow rate F of sap flowing in a tree is high (if the sap flow speed u is high), for example, the temperature difference ΔT between the respective temperature sensors of the probes HP and RP in a pair of the Granier sensor is small. This is because, while the heater applies constant heat to the heater-equipped temperature probe HP, this heat is carried away by a large quantity of sap flowing in the vicinity of the heater-equipped temperature probe HP. Meanwhile, if the sap flow rate F is low (if the sap flow speed u is low), the temperature difference ΔT between the respective temperature sensors of the probes HP and RP in a pair of the Granier sensor is large. This is because, while the heater applies constant heat to the heater-equipped temperature probe HP, this heat supplied to the heater-equipped temperature probe HP stays without being carried away by sap as the sap flows in small quantity in the vicinity of the heater-equipped temperature probe HP.

(Vascular Sap Measurement Sensor)

The configuration of the vascular sap measurement sensor 1 will be described next.

As shown in FIG. 1, the vascular sap measurement sensor 1 includes a support 10, a trapping probe 20, an electrical resistance probe 30, a heater-equipped temperature probe 40, and temperature probes 50A and 50B in a pair.

While all the probes 20, 30, 40, 50A, and 50B are aligned parallel to each other in the same horizontal plane, the base end of each of these probes 20, 30, 40, 50A, and 50B is supported on the support 10. The two temperature probes 50A and 50B in a pair are provided at positions between which the heater-equipped temperature probe 40 is located. The vascular sap measurement sensor 1 is installed on a plant by sticking the probes 20, 30, 40, 50A, and 50B into a stem as a new branch distal end of the plant.

The support 10 and the probes 20, 30, 40, 50A, and 50B are formed by processing a semiconductor substrate such as a silicon substrate or a silicon on insulator (SOI) substrate using the MEMS technology involving thin film formation by means of photolithography, etching, a sputtering process, or a vacuum deposition process, for example.

(Support)

The support 10 is a member that supports the probes 20, 30, 40, 50A, and 50B. The support 10 is a plate member rectangular in a plan view. All the probes 20, 30, 40, 50A, and 50B are supported on one long side part of the support 10. The support 10 has such a length in its long side direction as is required to allow all the probes 20, 30, 40, 50A, and 50B to be aligned at predetermined intervals. The length of the support 10 in its short side direction is not particularly limited.

Figure 2:
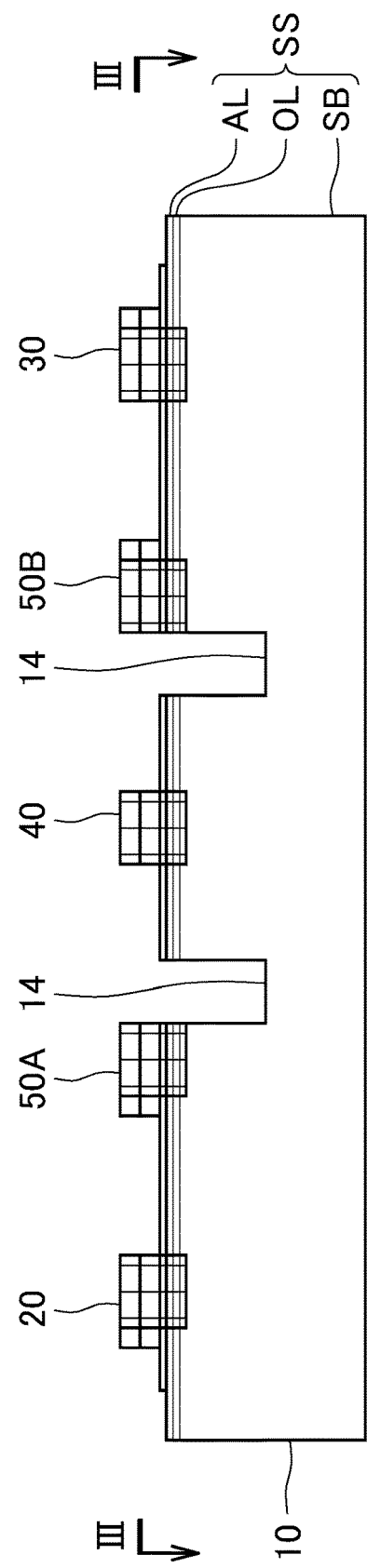
FIG. 2 is a front view of the vascular sap measurement sensor of FIG. 1.

As shown in FIG. 2, the support 10 is formed of a semiconductor substrate SS. For example, an SOI substrate or a silicon substrate is used as the semiconductor substrate SS. The SOI substrate has a three-layer structure including a support substrate SB, an active layer AL, and an oxide film layer OL caught between the support substrate SB and the active layer AL. The support substrate SB is made of silicon (Si) and has a thickness from 400 to 500 µm. The active layer AL is made of silicon (Si) and has a thickness of about 10 µm. The oxide film layer OL is made of silicon dioxide (SiO$_2$) and has a thickness from 0.1 to 1 µm. The active layer AL has heat conductivity. The oxide film layer OL is an insulator that lets little heat and electricity pass through.

(Probe)

As shown in FIG. 1, each of the probes 20, 30, 40, 50A, and 50B is a rod-shaped member formed in a cantilever shape at an edge (long side part) of the support 10. The tip portion of each of the probes 20, 30, 40, 50A, and 50B is preferably formed into a pointed shape such as a triangular shape. Forming the tip portion of each of the probes 20, 30, 40, 50A, and 50B into a pointed shape can reduce insertion resistance occurring when the probes 20, 30, 40, 50A, and 50B are inserted into a fine point of a plant. As a result, it becomes possible to smoothly stick and install the probes 20, 30, 40, 50A, and 50B into and on a stem as the fine point of the plant, for example. This can further prevent breakage of the tip portions of the probes 20, 30, 40, 50A, and 50B that is to occur when the probes 20, 30, 40, 50A, and 50B are stuck into the fine point of the plant.

Each of the probes 20, 30, 40, 50A, and 50B is formed into dimensions that allow each of these probes to be stuck into and installed on a fine point of a plant such as a new branch distal end or a pedicel of the plant having a stem diameter or an axis diameter of about several millimeters. Each of the probes 20, 30, 40, 50A, and 50B is formed into a length (a length in the axis direction of each of the probes from the base end to the tip of each of the probes) that allows a tip portion of the probe to be located in a xylem or a phloem at the fine point of the plant while the probe is stuck into and installed on this fine point of the plant. For example, each of the probes 20, 30, 40, 50A, and 50B has a length from 50 to 1,000 µm.

In the first embodiment, the electrical resistance probe 30 is formed into a greater length than the other probes 20, 40, 50A, and 50B. More specifically, the electrical resistance probe 30 is formed into a length greater than the other probes 20, 40, 50A, and 50B by an amount corresponding to a distance between the center of a phloem and the center of a xylem in a plant as a measurement target. This difference in length depends on the type of the plant as a measurement target or the diameter of a stem of the plant and is set to be from 50 to 300 µm, for example.

The width of each of the probes 20, 30, 40, 50A, and 50B is not particularly limited but may be from 50 to 300 µm, for example. Reducing the widths of the probes 20, 30, 40, 50A, and 50B can further alleviate damage (injury) to a plant.

Figure 4A:
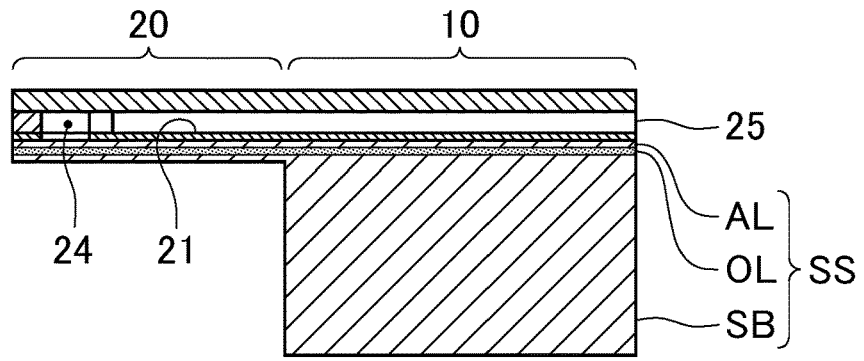
FIG. 4A is a sectional view taken along an arrowed line IVa-IVa of FIG. 1.
Figure 4B:
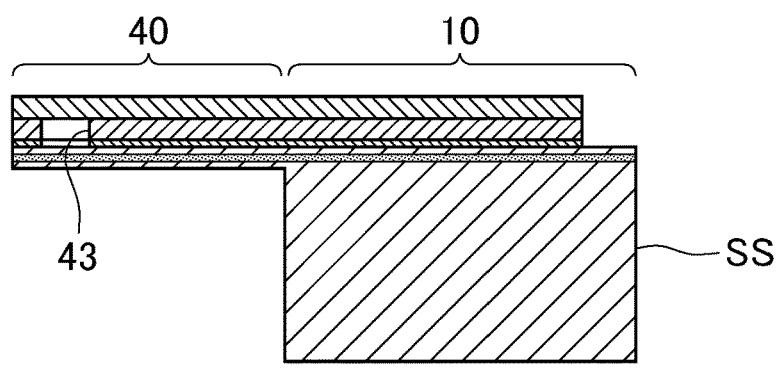
FIG. 4B is a sectional view taken along an arrowed line IVb-IVb of FIG. 1.
Figure 4C:
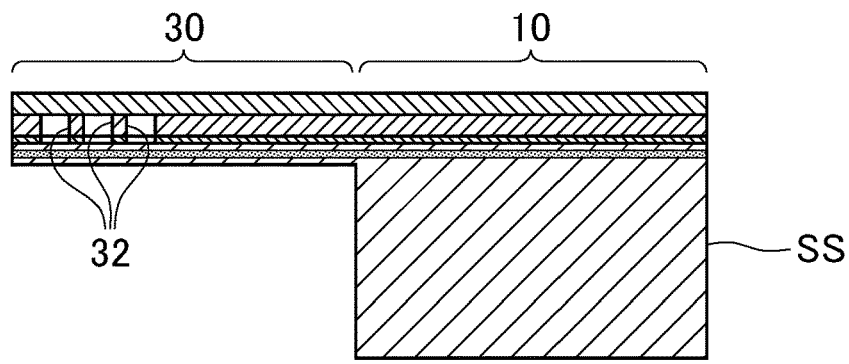
FIG. 4C is a sectional view taken along an arrowed line IVc-IVc of FIG. 1.

As shown in FIGS. 4A, 4B, and 4C, each of the probes 20, 30, 40, 50A, and 50B is made thinner than the support 10 by removing a lower part of the support substrate SB forming the SOI substrate SS. Each of the probes 20, 30, 40, 50A, and 50B is formed into a thickness smaller than the width of a phloem or that of a xylem in a plant as a measurement target. The thickness of each of the probes 20, 30, 40, 50A, and 50B depends on the type of the plant as a measurement target or the diameter of a stem of the plant and is from 50 to 300 µm, for example. A thickness not falling below 50 µm achieves sufficient strength, so that the probes 20, 30, 40, 50A, and 50B are free from the risk of being bent during insertion and extraction into and from a stem of the plant, for example. Further, a xylem and a phloem have diameters from about 100 to about 400 µm, though these diameters depend on the type of the plant. Thus, with a thickness not exceeding 300 µm, when the probes 20, 30, 40, 50A, and 50B are stuck into the xylem or the phloem, the probes can be prevented from being blocked.

(Trapping Probe)

The trapping probe 20 is a probe for trapping vascular sap such as phloem sap or xylem sap, and includes a trapping flow channel 21 that receives incoming flow of the vascular sap.

Figure 3:
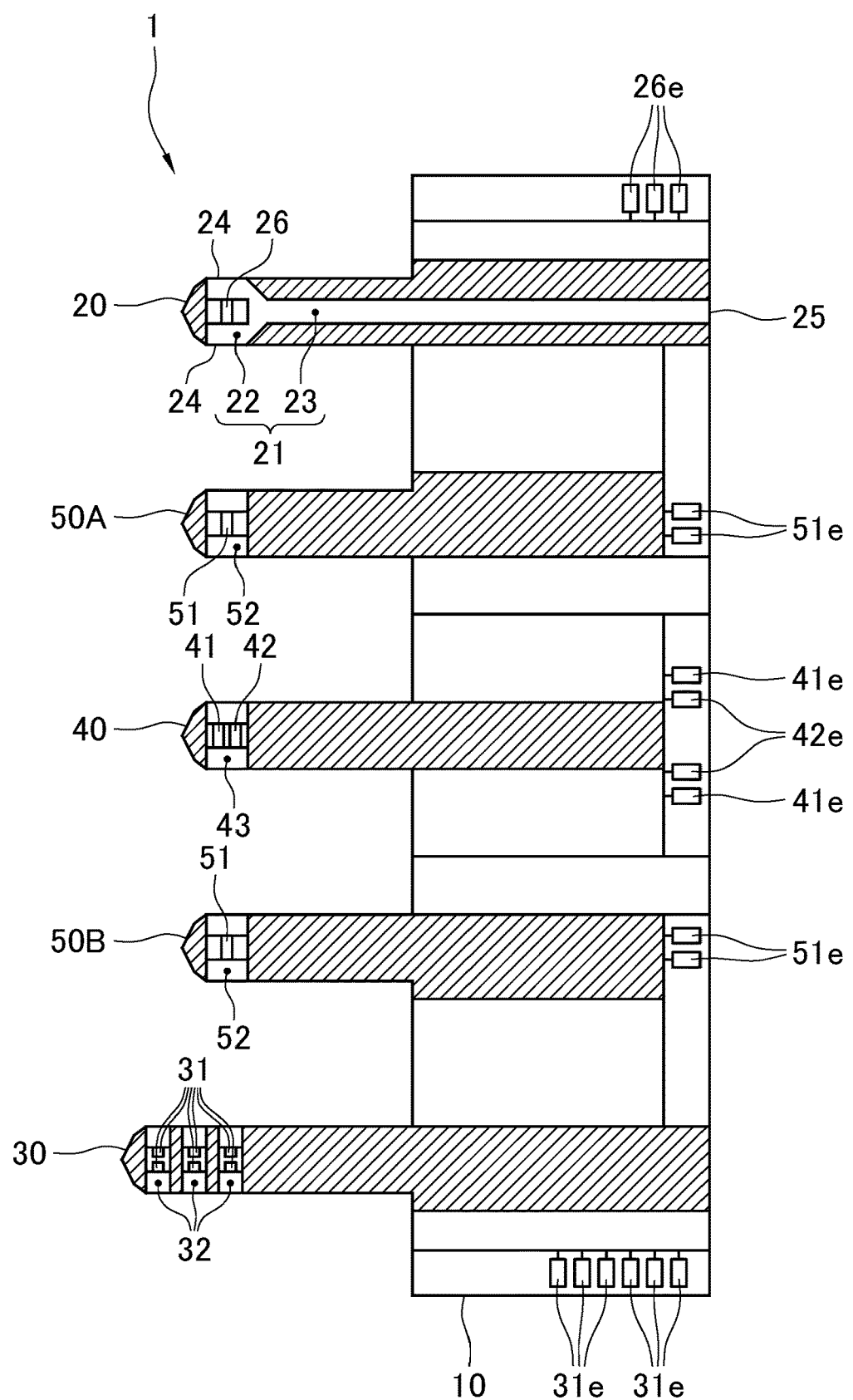
FIG. 3 is a sectional view taken along an arrowed line III-III of FIG. 2.

As shown in FIGS. 3 and 4A, the trapping flow channel 21 is formed in the trapping probe 20. FIG. 3 is a plan view in which a ceiling part 13 (described later) forming the trapping flow channel 21 is removed. The trapping flow channel 21 as a whole is substantially T-shaped, and includes a first flow channel 22 and a second flow channel 23. The trapping flow channel 21 has two inlet openings 24 and 24. The two inlet openings 24 and 24 are provided at a tip portion of the trapping probe 20. One of the inlet openings 24 is arranged on one side surface of the trapping probe 20. The other inlet opening 24 is arranged on the other side surface of the trapping probe 20. The first flow channel 22 connects the two inlet openings 24 and 24 and extends in the width direction of the trapping probe 20. The second flow channel 23 has one end connected to the first flow channel 22 and extends in the axis direction of the trapping probe 20.

The second flow channel 23 extends into the support 10 to reach an edge opposite an edge where the trapping probe 20 is provided. The trapping flow channel 21 has an outlet opening 25 provided on the back of the support 10. Vascular sap flowing into the trapping flow channel 21 can be trapped by a method such as connecting a tube to the outlet opening 25 and connecting a syringe to the other end of the tube.

Figure 5:
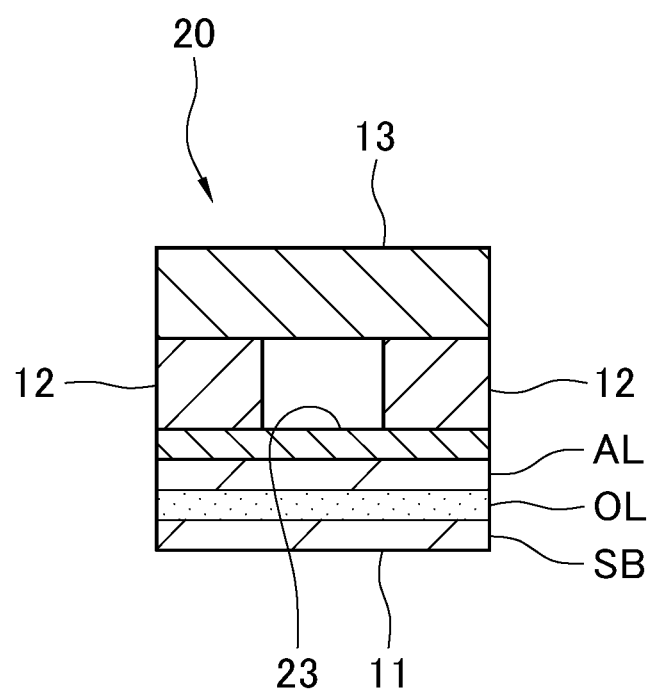
FIG. 5 is an enlarged sectional view taken along an arrowed line V-V of FIG. 1.

As shown in FIG. 5, the trapping probe 20 is rectangular in a cross section. The rectangular second flow channel 23 is formed in a substantially central area of the trapping probe 20. More specifically, the area where the second flow channel 23 is formed in the trapping probe 20 is defined by a bottom part 11, side walls 12 and 12 in a pair standing at opposite side parts of the bottom part 11, and the ceiling part 13 stretching across the upper ends of the side walls 12 and 12 in a pair.

The bottom part 11 is configured using the active layer AL, the oxide film layer OL, and a surface layer of the support substrate SB of the SOI substrate SS. This provides the bottom part 11 with a certain degree of thickness to allow increase in the strength of the trapping probe 20.

As shown in FIG. 3, a pH measurement element 26 is provided in the first flow channel 22. The pH measurement element 26 is an element for measuring the pH of vascular sap in a plant such as phloem sap or xylem sap. The pH measurement element 26 is not particularly limited, as long as it has a size installable on the tip portion of the trapping probe 20. For example, an ion sensitive field effect transistor (ISFET) is usable as the pH measurement element 26. The ion sensitive field effect transistor does not include a metal electrode part to be provided on a gate oxide film of a normal field effect transistor (FET) but it alternatively includes an ion sensitive film made of a dielectric material, for example.

The support 10 has an upper surface on which three electrode pads 26e connected to the pH measurement element 26 via interconnect lines (not shown) are provided. The three electrode pads 26e are connected to corresponding ones of a gate electrode, a source electrode, and a drain electrode of the pH measurement element 26.

In the ion sensitive field effect transistor, a potential at the ion sensitive film changes in a manner that depends on an ion concentration in vascular sap in contact with the ion sensitive film. This potential change is measured from a relationship between a voltage in the gate electrode and a current in the drain electrode. The pH of the vascular sap can be determined from the measured potential change.

(Electrical Resistance Probe)

The electrical resistance probe 30 is a probe with an electrical resistance measurement electrode 31 for measuring an electrical resistance in phloem sap or xylem sap.

As shown in FIGS. 3 and 4C, the electrical resistance probe 30 has a tip portion in which three electrode flow channels 32 are formed. Each electrode flow channel 32 extends in the width direction of the electrical resistance probe 30 and has openings arranged on opposite side surfaces of the electrical resistance probe 30. Thus, by sticking the electrical resistance probe 30 into a stem of a plant, for example, vascular sap is caused to flow into the electrode flow channel 32. The electrode flow channel 32 may be configured in such a manner that, while one of the openings is closed, the other opening is arranged on one of the side surfaces of the electrical resistance probe 30.

Like the trapping flow channel 21, the electrode flow channel 32 is defined by the bottom part 11, the side walls 12 and 12 in a pair standing at the opposite side parts of the bottom part 11, and the ceiling part 13 stretching across the upper ends of the side walls 12 and 12 in a pair.

The three electrode flow channels 32 are aligned in the axis direction of the electrical resistance probe 30. Electrical resistance measurement electrodes 31 and 31 in a pair are provided in each of the three electrode flow channels 32. In this way, the electrical resistance measurement electrodes 31 in three pairs are aligned in units of pairs in the axis direction of the electrical resistance probe 30.

The electrical resistance measurement electrodes 31 and 31 in a pair are electrodes for measuring an electrical resistance in a substance existing between these electrical resistance measurement electrodes 31 and 31 in a pair such as phloem sap or xylem sap in a plant, for example. As long as the electrical resistance measurement electrode 31 can be arranged at the tip portion of the electrical resistance probe 30, the size of the electrical resistance measurement electrode 31 is not particularly limited. For example, an aluminum thin film is usable as the electrical resistance measurement electrode 31.

Electrode pads 31e connected to corresponding ones of the electrical resistance measurement electrodes 31 via interconnect lines (not shown) are arranged on the upper surface of the support 10. A power supply is connected between the electrode pads 31e and 31e in a pair for corresponding ones of the electrical resistance measurement electrodes 31 and 31 in a pair. A current is supplied between the electrical resistance measurement electrodes 31 and 31 in a pair from the power supply, and the current flowing between the electrical resistance measurement electrodes 31 and 31 in a pair is measured using an ammeter. According to Ohm's law, an electrical resistance between the electrical resistance measurement electrodes 31 and 31 in a pair can be calculated from the current measured using the ammeter.

The number of the electrode flow channels 32 provided at one electrical resistance probe 30 is not particularly limited. One, or two or more electrode flow channels 32 may be provided. The number of the electrical resistance measurement electrodes 31 provided at one electrical resistance probe 30 is not particularly limited. The electrical resistance measurement electrodes 31 may be provided in one pair, or two or more pairs.

(Heater-Equipped Temperature Probe)

The heater-equipped temperature probe 40 is a probe including a temperature sensor 41 and a heater 42 used in the Granier method.

As shown in FIGS. 3 and 4B, the heater-equipped temperature probe 40 has a tip portion in which a temperature sensor flow channel 43 is formed. The temperature sensor flow channel 43 extends in the width direction of the heater-equipped temperature probe 40 and has openings arranged on opposite side surfaces of the heater-equipped temperature probe 40. Thus, by sticking the heater-equipped temperature probe 40 into a stem of a plant, for example, vascular sap is caused to flow into the temperature sensor flow channel 43. The temperature sensor flow channel 43 may be configured in such a manner that, while one of the openings is closed, the other opening is arranged on one of the side surfaces of the heater-equipped temperature probe 40. In this case, however, a way in which the vascular sap flows changes to bring about the necessity to modify the formula 1 partially.

Like the trapping flow channel 21, the temperature sensor flow channel 43 is defined by the bottom part 11, the side walls 12 and 12 in a pair standing at the opposite side parts of the bottom part 11, and the ceiling part 13 stretching across the upper ends of the side walls 12 and 12 in a pair.

The temperature sensor 41 and the heater 42 are provided in the temperature sensor flow channel 43. The temperature sensor 41 has a function of sensing a temperature. As long as the temperature sensor 41 can be arranged at the tip portion of the heater-equipped temperature probe 40, the size of the temperature sensor 41 is not particularly limited. For example, a pn-junction diode formed using an oxidation and diffusion furnace is usable as the temperature sensor 41.

Electrode pads 41e and 41e in a pair connected to the temperature sensor 41 via interconnect lines (not shown) are arranged on the upper surface of the support 10. The temperature sensor 41 (pn junction diode of the temperature sensor 41) has terminals connected via interconnect lines not shown to corresponding ones of the electrode pads 41e.

The forward characteristics of a diode change with temperature. This temperature change is known to change a voltage in response to flow of a constant current in the diode. A constant current source is connected between the electrode pads 41e and 41e in a pair. A constant current is supplied in a forward direction from the constant current source to the temperature sensor 41 as a pn junction diode, and a voltage between the anode and the cathode of the temperature sensor 41 is measured using a voltmeter. A temperature can be calculated from the voltage measured using the voltmeter.

The heater 42 can function to supply heat to the heater-equipped temperature probe 40. As long as the heater 42 can be provided at the heater-equipped temperature probe 40, the size of the heater 42 is not particularly limited. For example, a pn-junction diode formed using an oxidation and diffusion furnace is usable as the heater 42. The heater 42 may also be formed by forming a thin film of platinum (Pt), nichrome (NiCr), or an indium tin oxide material (ITO) by deposition or sputtering, and processing the thin film into a predetermined shape. The heater 42 is not always required to be provided in the temperature sensor flow channel 43 but can be provided in any position where the heater 42 can supply heat to the heater-equipped temperature probe 40.

Electrode pads 42e and 42e in a pair connected to the heater 42 via interconnect lines (not shown) are arranged on the upper surface of the support 10. The heater 42 (pn junction diode of the heater 42) has terminals connected via interconnect lines not shown to corresponding ones of the electrode pads 42e.

A DC constant voltage source is connected between the electrode pads 42e and 42e in a pair. The DC constant voltage source supplies a constant voltage in a forward direction to the heater 42 as a pn junction diode. Heat can be generated by flowing a current in the heater 42.

(Temperature Probe)

Each of the temperature probes 50A and 50B is a probe including a temperature sensor 51 used in the Granier method.

As shown in FIG. 3, each of the temperature probes 50A and 50B has a tip portion in which a temperature sensor flow channel 52 is formed. The temperature sensor flow channel 52 extends in the width direction of each of the temperature probes 50A and 50B and has openings arranged on opposite side surfaces of each of the temperature probes 50A and 50B. Thus, by sticking each of the temperature probes 50A and 50B into a stem of a plant, for example, vascular sap is caused to flow into the temperature sensor flow channel 52. The temperature sensor flow channel 52 may be configured in such a manner that, while one of the openings is closed, the other opening is arranged on one of the side surfaces of each of the temperature probes 50A and 50B.

Like the trapping flow channel 21, the temperature sensor flow channel 52 is defined by the bottom part 11, the side walls 12 and 12 in a pair standing at the opposite side parts of the bottom part 11, and the ceiling part 13 stretching across the upper ends of the side walls 12 and 12 in a pair.

The temperature sensor 51 is provided in the temperature sensor flow channel 52. The temperature sensor 51 can be a sensor similar to the temperature sensor 41 of the heater-equipped temperature probe 40.

Electrode pads 51e and 51e in a pair connected to the temperature sensor 51 via interconnect lines (not shown) are arranged on the upper surface of the support 10. The temperature sensor 51 can be used in the same way as the temperature sensor 41 of the heater-equipped temperature probe 40 for measuring a temperature.

As shown in FIG. 2, a groove 14 is formed between a part of the support 10 supporting the heater-equipped temperature probe 40 and each part of the support 10 supporting each of the temperature probes 50A and 50B. The groove 14 is formed by removing the active layer AL, the oxide film layer OL, and an upper part of the support substrate SB of the SOI substrate SS. Alternatively, the groove 14 may be formed by removing only the active layer AL.

By the presence of the groove 14 formed between the heater-equipped temperature probe 40 and each of the temperature probes 50A and 50B, the heater-equipped temperature probe 40 and each of the temperature probes 50A and 50B become connected to each other via the oxide film layer OL having high heat insulating property. Specifically, the heater-equipped temperature probe 40 and each of the temperature probes 50A and 50B are thermally separated from each other. This makes it unlikely that heat of the heater 42 of the heater-equipped temperature probe 40 will be transmitted via the support 10 to each of the temperature probes 50A and 50B. As a result, the temperature of vascular sap can be measured with high accuracy using the temperature sensor 51 of each of the temperature probes 50A and 50B, making it possible to determine the flow speed of the vascular sap with high accuracy and determine a flow rate from the determined flow speed with high accuracy.

(Method of Use)

A method of using the vascular sap measurement sensor 1 will be described next.

(Attachment)

First, the vascular sap measurement sensor 1 is attached to a new branch distal end of a plant as a measurement target.

Figure 6:
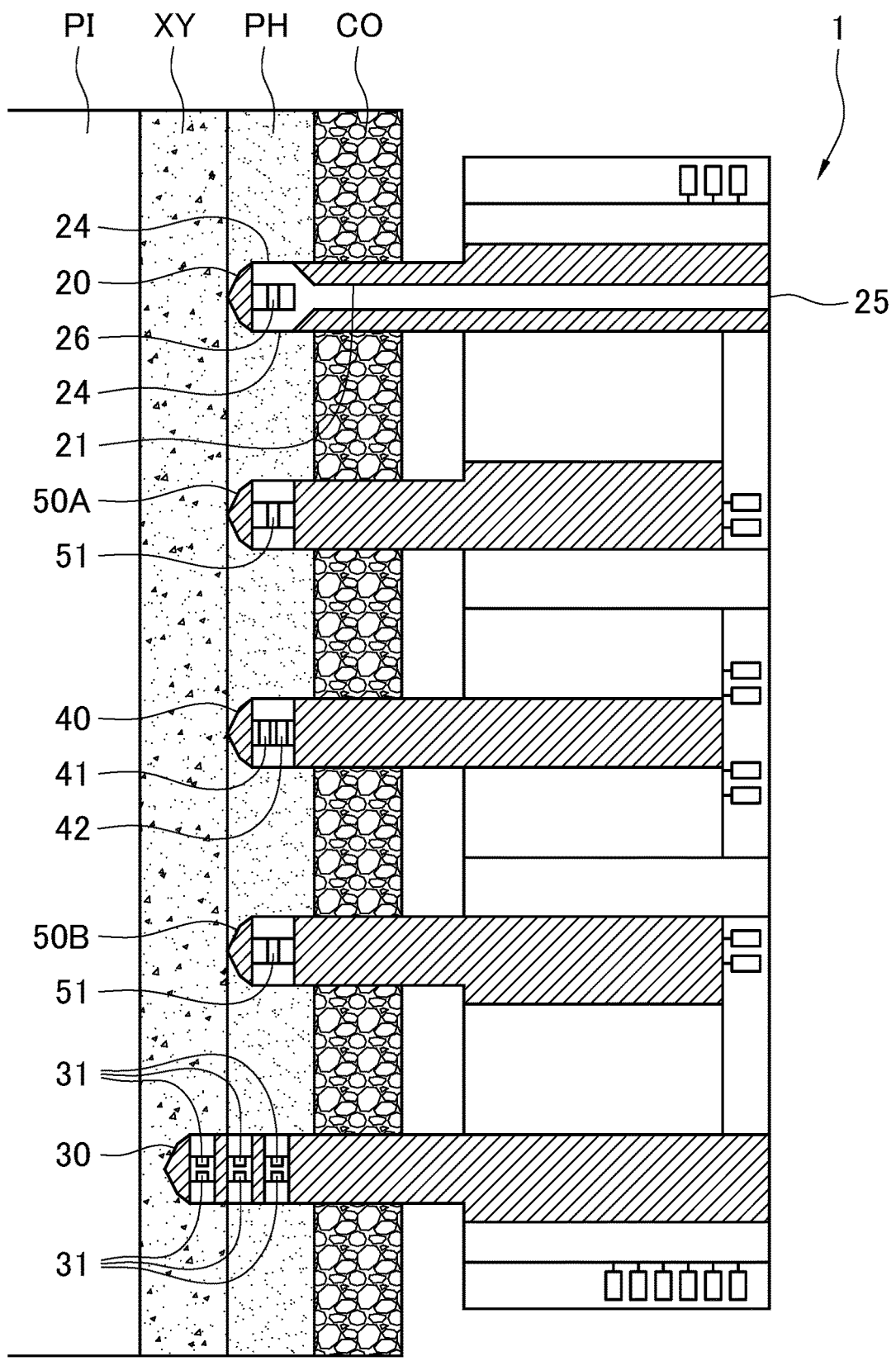
FIG. 6 explains a condition of use of the vascular sap measurement sensor of FIG. 1.

More specifically, as shown in FIG. 6, the vascular sap measurement sensor 1 is attached by sticking all the probes 20, 30, 40, 50A, and 50B of the vascular sap measurement sensor 1 into a fine point of the plant such as a stem. At this time, the probes 20, 30, 40, 50A, and 50B are located along a xylem XY and a phloem PH.

As the probes 20, 30, 40, 50A, and 50B are stuck into the fine point of the plant such as the stem, the electrical resistance measurement electrode 31 provided at the electrical resistance probe 30 passes through a cortical layer CO and the phloem PH in the plant to reach the xylem XY. As the probes 20, 30, 40, 50A, and 50B are stuck more deeply, the electrical resistance measurement electrode 31 reaches a pith PI of the plant.

Xylem sap flowing in the xylem XY contains minerals, so that it has the property of being lower in electrical resistance than water in the other parts (including cortical layer CO, phloem PH, pith PI, and the like). By using this property, the position of the xylem XY can be detected from an electrical resistance measured by the electrical resistance probe 30. In particular, in the first embodiment, the electrical resistance measurement electrodes 31 in three pairs are aligned in the axis direction of the electrical resistance probe 30. This makes it possible to provide a distribution of electrical resistances in the plant, so that the position of the xylem XY can be determined precisely.

The electrical resistance measurement electrode 31 is provided in the electrode flow channel 32. Even if tissues between the xylem XY and the phloem PH are destroyed by sticking the electrical resistance probe 30 into the stem of the plant, for example, mixing of xylem sap and phloem sap can be suppressed in the electrode flow channel 32. The electrical resistance measurement electrode 31 can measure a pure electrical resistance in the xylem sap or the phloem sap to obtain a large difference between the electrical resistance measured in the xylem XY and an electrical resistance measured in a different part. This achieves high detection accuracy of the position of the xylem XY.

Depths of sticking of the probes 20, 30, 40, 50A, and 50B can be adjusted based on the detected position of the xylem XY. The respective tip portions of the trapping probe 20, the heater-equipped temperature probe 40, and the temperature probes 50A and 50B can be located in the phloem PH or in the xylem XY.

The pH measurement element 26 provided at the trapping probe 20 is usable for measuring the pH value of vascular sap. Phloem sap contains a photosynthesis product such as sucrose, so that it has a higher pH value than xylem sap. More particularly, while the xylem sap has pH of generally about 6, the phloem sap has a pH value from about 7.5 to about 8. Whether vascular sap having flowed into the trapping flow channel 21 in the trapping probe 20 is phloem sap or xylem sap can be determined based on the pH value measured by the pH measurement element 26. Sticking the probes 20, 30, 40, 50A, and 50B until the pH value measured by the pH measurement element 26 becomes equal to the pH value of the phloem sap makes it possible to locate the tip portion of the trapping probe 20 in the phloem PH.

(Trapping of Vascular Sap)

The vascular sap measurement sensor 1 traps vascular sap as follows.

Locating the tip portion of the trapping probe 20 in the phloem PH in a plant causes phloem sap to flow into the trapping flow channel 21. The phloem sap having flowed into the trapping flow channel 21 can be collected with a syringe connected to the outlet opening 25, for example.

Locating the tip portion of the trapping probe 20 in the xylem XY allows collection of xylem sap.

The trapped vascular sap is carried back to a laboratory, for example, and analyzed using a device such as a liquid chromatography device. By doing so, the vascular sap can be analyzed in terms of a nutritive substance, etc. In this way, the trapping probe 20 is usable for trapping the vascular sap and for analyzing a nutritive substance in the vascular sap accordingly.

The inlet opening 24 of the trapping flow channel 21 is arranged on the side surface of the trapping probe 20. This makes it unlikely that the trapping flow channel 21 will be blocked by tissues of a plant when sticking the trapping probe 20 into the plant.

The inlet openings 24 of the trapping flow channel 21 are arranged on the opposite side surfaces of the trapping probe 20. This allows trapping of the vascular sap from either side of the trapping probe 20. In particular, while the direction of a phloem flow cannot be grasped from the outer shape of a plant, this configuration makes it possible to trap the phloem sap without the need of caring for the direction of the phloem flow.

The inlet opening 24 of the trapping flow channel 21 is arranged on the side surface of the trapping probe 20. This prevents mixing of the xylem sap and the phloem sap to allow retrieval of pure phloem sap or xylem sap. Unlike a process using aphids, an intake port is not exposed to the outside world. This allows retrieval of highly pure phloem sap or xylem sap and provides suitability for long-term monitoring.

(Dynamics of Vascular Sap)

The vascular sap measurement sensor 1 measures the dynamics of vascular sap as follows.

First, the respective tip portions of the heater-equipped temperature probe 40 and the temperature probes 50A and 50B are located in the phloem PH in a plant. Next, the heater 42 provided at the heater-equipped temperature probe 40 is started. By starting the heater 42, heat energy from the heater 42 is supplied to the heater-equipped temperature probe 40. The heat energy supplied to the heater-equipped temperature probe 40 is emitted from a surface of the heater-equipped temperature probe 40 to phloem sap flowing in the phloem PH.

At this time, the temperature of the heater-equipped temperature probe 40 and those of the temperature probes 50A and 50B are measured by the temperature sensors 41 and 51. The direction of a phloem flow can be determined by comparing temperatures measured at the two temperature probes 50A and 50B for the following reason.

The two temperature probes 50A and 50B are provided at positions between which the heater-equipped temperature probe 40 is located. Thus, if the phloem sap flows from a distal end toward a root of the plant, the temperature probe 50B closer to the root is warmed by the phloem sap increased in temperature by the heater-equipped temperature probe 40 to be at a higher temperature than the temperature probe 50A closer to the distal end.

Conversely, if the phloem sap flows from the root toward the distal end of the plant, the temperature probe 50A closer to the distal end is warmed by the phloem sap increased in temperature by the heater-equipped temperature probe 40. Thus, a temperature detected at the temperature probe 50A is higher than that detected at the temperature probe 50B closer to the root.

Specifically, the direction of the phloem flow can be determined to be from the temperature probe 50A or 50B at a lower temperature toward the temperature probe 50B or 50A at a higher temperature.

Next, based on the temperatures measured at the heater-equipped temperature probe 40 and the temperature probes 50A and 50B, the flow rate (flow speed) of the phloem flow in a new branch distal end is measured according to the aforementioned Granier method. Here, the flow rate (flow speed) is calculated based on a temperature difference between the temperature probe 50A or 50B at a lower temperature out of the two temperature probes 50A and 50B and the heater-equipped temperature probe 40. This is because the temperature probe 50A or 50B at a lower temperature is located on an upstream side of the phloem flow relative to the heater-equipped temperature probe 40.

If the flow rate of the phloem flow is high (if the flow speed thereof is high), for example, phloem sap in the vicinity of the heater-equipped temperature probe 40 is always replaced by new phloem sap. Thus, if constant heat energy is supplied to the heater-equipped temperature probe 40, the temperature of the heater-equipped temperature probe 40 is taken away by the phloem sap in the vicinity of the heater-equipped temperature probe 40. By contrast, if the flow rate of the phloem flow is low (if the flow speed thereof is low), phloem sap stays in the vicinity of the heater-equipped temperature probe 40. Thus, if constant heat energy is supplied to the heater-equipped temperature probe 40, the temperature of the heater-equipped temperature probe 40 is accumulated.

In this way, the flow speed and the flow rate of the phloem flow can be calculated by measuring the temperature difference $\Delta T$ between the heater-equipped temperature probe 40 and the temperature probe 50A or 50B. Locating the respective tip portions of the heater-equipped temperature probe 40 and the temperature probes 50A and 50B in the xylem XY in the plant makes it possible to determine the flow speed and the flow rate of a xylem flow.

The temperature sensor 41 of the heater-equipped temperature probe 40 is provided in the temperature sensor flow channel 43. Even if tissues between the xylem XY and the phloem PH are destroyed by sticking the heater-equipped temperature probe 40 into the plant, mixing of xylem sap and phloem sap can be suppressed in the temperature sensor flow channel 43. Further, the temperature sensor 51 of each of the temperature probes 50A and 50B is provided in the temperature sensor flow channel 52. Even if tissues between the xylem XY and the phloem PH are destroyed by sticking the temperature probe 50A or 50B into the plant, mixing of the xylem sap and the phloem sap can be suppressed in the temperature sensor flow channel 52.

The flow speed of a phloem flow is generally lower by about one order of magnitude than the flow speed of a xylem flow. Hence, the mixing of xylem sap and phloem sap makes it impossible to measure a flow rate precisely. In this regard, the mixing of the xylem sap and the phloem sap can be suppressed in the first embodiment, making it possible to measure a vascular sap flow rate precisely.

The vascular sap measurement sensor 1 is formed of the semiconductor substrate SS. This can reduce the size of the vascular sap measurement sensor 1, so that each of the probes 20, 30, 40, 50A, and 50B can be formed into a minute size. Thus, even when the vascular sap measurement sensor 1 is installed on a plant, damage (injury) to the plant can be alleviated. Thus, the vascular sap measurement sensor 1 can be installed for a long period of time. As a result, the dynamics of vascular sap in the plant can be monitored for a long period of time, so that the plant can be supplied with water or replenished with nutrients (fertilized) appropriately in a manner that conforms to the growing condition of the plant.

Each of the probes 20, 30, 40, 50A, and 50B is formed into a minute size. Thus, even if the probes 20, 30, 40, 50A, and 50B are installed on a plant by being stuck into the plant, stress on the plant can be alleviated. In other words, reduction can be achieved in a change between before installation and after installation of the probes 20, 30, 40, 50A, and 50B with regard to the dynamics of vascular sap in the place of installation in the plant. This makes it possible to measure the dynamics of the vascular sap flowing in the place of the installation immediately after the probes 20, 30, 40, 50A, and 50B are installed on the plant. Additionally, while a conventional sensor is hard to install on a fine point of a plant such as a new branch distal end or a pedicel, the probes 20, 30, 40, 50A, and 50B can be attached to such a fine point easily.

By measuring the dynamics of vascular sap in a plant using the vascular sap measurement sensor 1, the plant can be supplied with water or replenished with nutrients at the most appropriate times in accordance with the growing condition of the plant. This can contribute to increase in harvest of crops or fruit, and the like. Further, a water quantity in a new branch distal end or a pedicel of the plant can be measured, so that water supply can be controlled properly (water resources can be used effectively). This achieves high-value added cultivation of fruit in terms of a high quality (high sugar content in a fruit) or stable production (equal quality), for example.

(Manufacturing Method)

A method of manufacturing the vascular sap measurement sensor 1 will be described next based on FIGS. 7 to 15.

To form the vascular sap measurement sensor 1 using the semiconductor substrate SS by means of the MEMS technology, a large number of vascular sap measurement sensors 1 are generally formed together using a disk-shaped substrate having a size such as a 12-inch size or an 8-inch size, for example. By using such a manufacturing method, manufacturing cost for one vascular sap measurement sensor 1 can be reduced considerably. Meanwhile, for the sake of convenience of the description, formation of one vascular sap measurement sensor 1 will be explained below and illustrated in the drawings. For manufacture of a large number of vascular sap measurement sensors 1 together using a disk-shaped substrate, a similar procedure is basically followed. In this case, however, after the large number of vascular sap measurement sensors 1 are formed on the substrate, a step of dicing and separating is required for forming the individual vascular sap measurement sensors 1.

(1) Preparatory Step

Figure 7A:
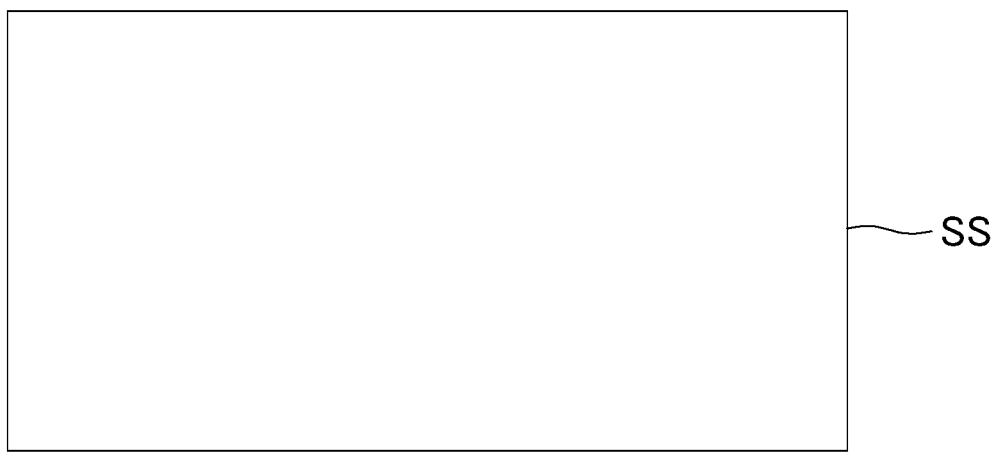
FIG. 7A is a plan view of the vascular sap measurement sensor in a preparatory step.
Figure 7B:
FIG. 7B is a front view of this vascular sap measurement sensor.

As shown in FIGS. 7A and 7B, the semiconductor substrate SS is prepared. In the example described below, an SOI substrate is used as the semiconductor substrate SS. Meanwhile, substantially similar steps are followed in the case of using a silicon substrate.

The SOI substrate SS before being processed is a thin plate rectangular in a plan view. In a preparatory step, a surface of the SOI substrate SS is cleaned first with a chemical. Next, a thermally oxidized film is formed on the surface of the SOI substrate SS using an oxidation and diffusion furnace. As long as an oxide film is formed on the surface of the SOI substrate SS, the thermally oxidized film may be replaced by an oxide film formed by thin film formation technology.

(2) Sensor Unit Forming Step

Figure 8A:
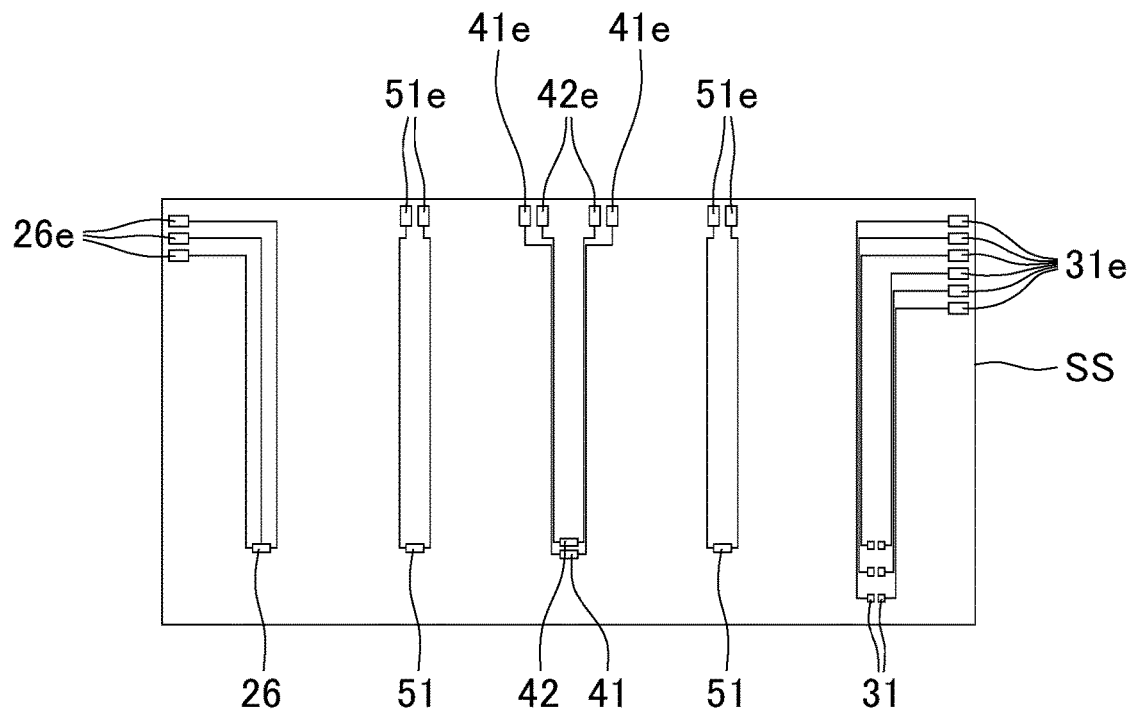
FIG. 8A is a plan view of the vascular sap measurement sensor in a sensor unit forming step.
Figure 8B:
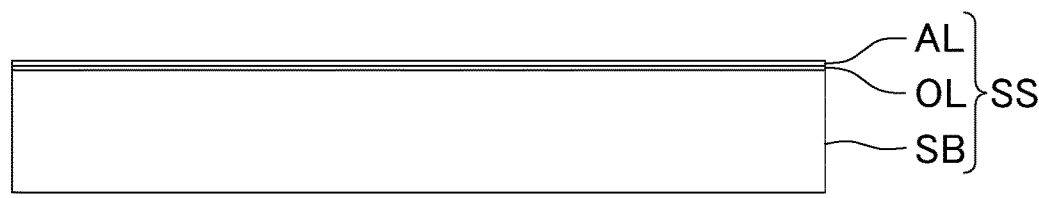
FIG. 8B is a front view of this vascular sap measurement sensor.

Next, as shown in FIGS. 8A and 8B, a sensor unit is formed on the thermally oxidized film on the surface of the SOI substrate SS. The sensor unit includes the pH measurement element 26, the electrical resistance measurement electrode 31, the temperature sensors 41 and 51, the heater 42, the electrode pads 26e, 31e, 41e, 42e, and 51e, and interconnect lines.

The ion sensitive field effect transistor as the pH measurement element 26 has the basic configuration of an MOS field effect transistor (MOS-FET). The ion sensitive field effect transistor is formed by the following procedure. A layer with a built-in source and a layer with a built-in drain ($n^+$) are formed on the active layer AL (p type) of the SOI substrate SS by a diffusion step, for example. Next, a metal electrode to be connected to these layers of the built-in source and drain is formed by a sputtering process or a deposition process. Then, an ion sensitive film (gate oxide film) made of a dielectric film such as $SiO_2$ or $TaO_x$ is formed on these layers and the metal electrode by a sputtering process, for example.

pn junction diodes as the temperature sensors 41 and 51, and the heater 42 are formed by providing a hole (p type) for diffusion on the SOI substrate SS and then forming n diffusion (n type).

The electrical resistance measurement electrode 31, the electrode pads 26e, 31e, 41e, 42e, and 51e, and the interconnect lines are formed by depositing an Al thin film on the SOI substrate SS using a sputtering process or a deposition process, for example.

(3) Protective Film Forming Step

Figure 9A:
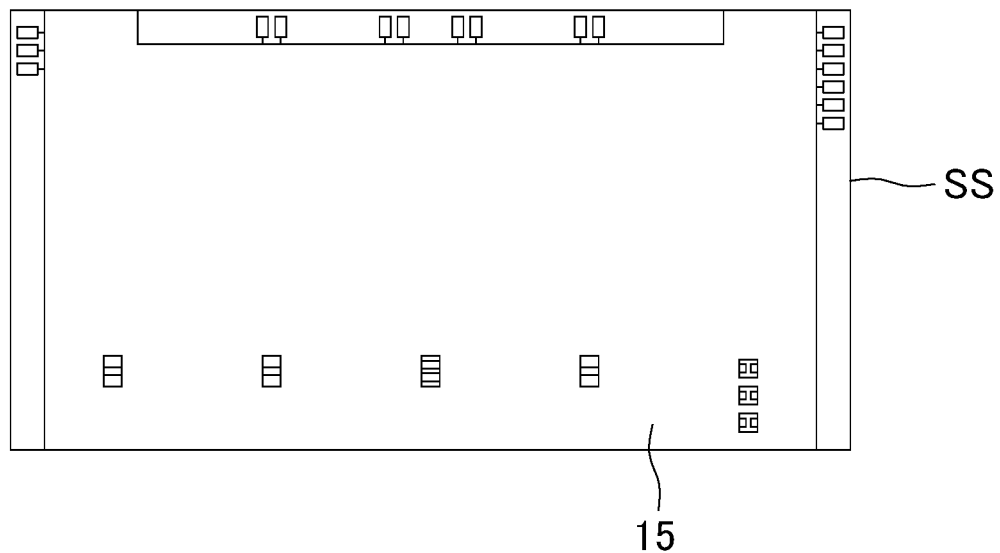
FIG. 9A is a plan view of the vascular sap measurement sensor in a protective film forming step.
Figure 9B:
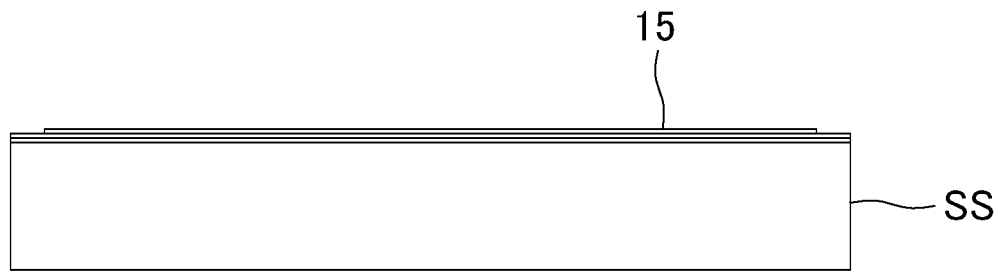
FIG. 9B is a front view of this vascular sap measurement sensor.

Next, as shown in FIGS. 9A and 9B, a photoresist is applied to the surface of the SOI substrate SS. Then, the photoresist is subjected to exposure and development to remove an unnecessary part of the photoresist, thereby forming a protective film 15 covering the interconnect lines in the sensor unit. Alternatively, the protective film 15 may be formed by providing a layer of an insulating material such as $SiO_2$ or $Si_3N_4$ by thin film technology and then processing the resultant layer into an intended shape through exposure and an etching process.

(4) Probe Forming Step

Figure 10A:
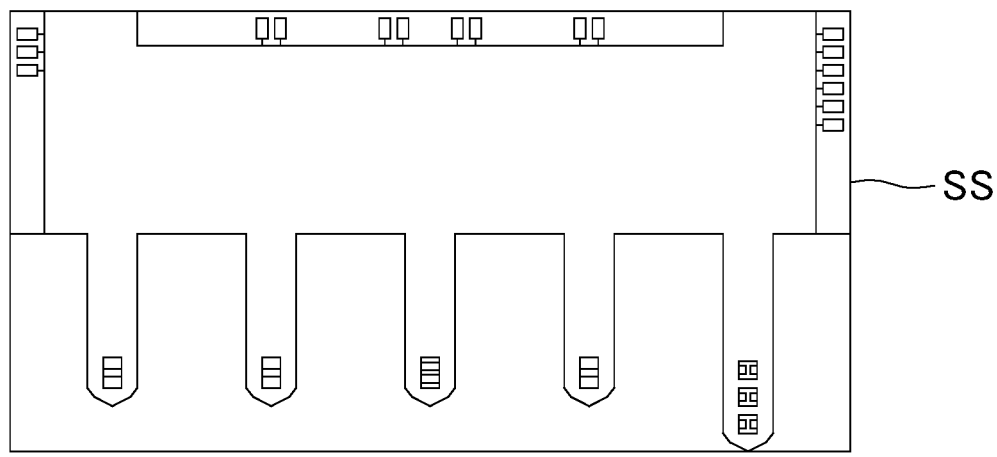
FIG. 10A is a plan view of the vascular sap measurement sensor in a probe forming step (first half).
Figure 10B:
FIG. 10B is a front view of this vascular sap measurement sensor.

Next, as shown in FIGS. 10A and 10B, photolithography is performed into probe shapes on the SOI substrate SS. Then, an unnecessary part is removed by dry etching such as ICP-RIE, thereby forming prototypes of the probe shapes. In this step, the active layer AL, the oxide film layer OL, and the upper part of the support substrate SB of the SOI substrate SS are removed.

Figure 11A:
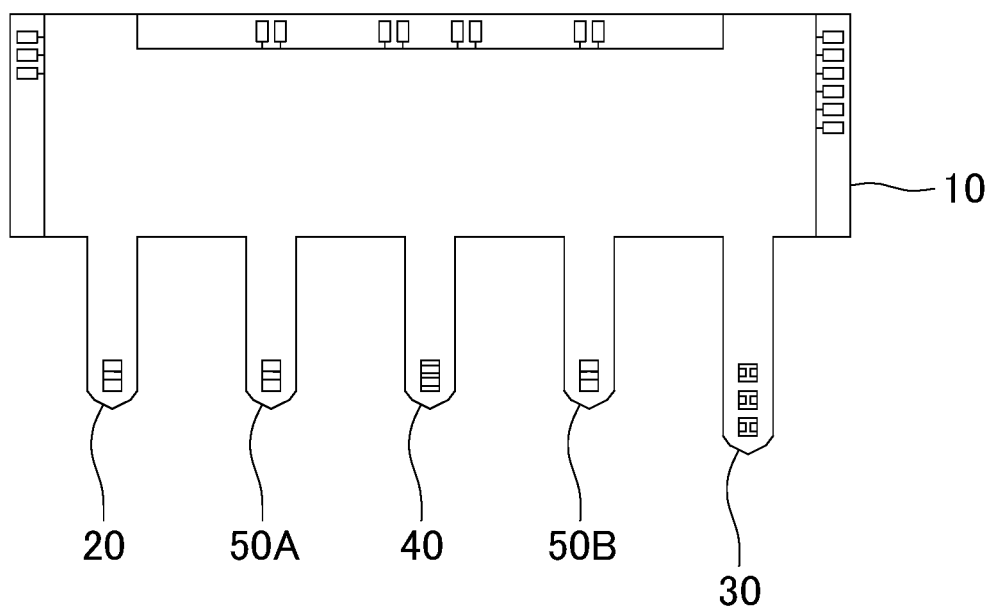
FIG. 11A is a plan view of the vascular sap measurement sensor in the probe forming step (latter half).
Figure 11B:
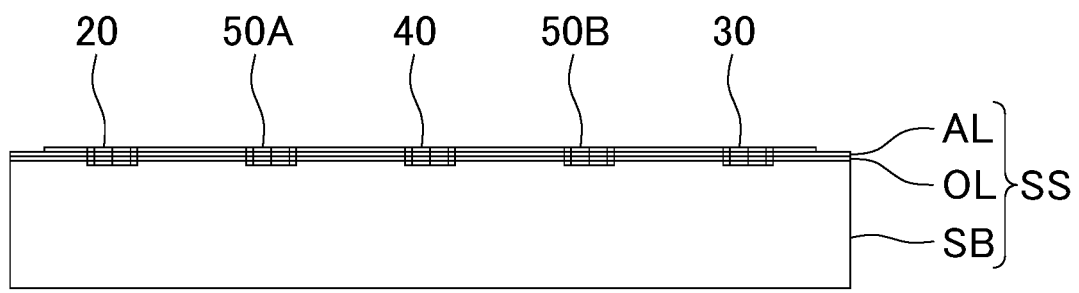
FIG. 11B is a front view of this vascular sap measurement sensor.

Then, as shown in FIGS. 11A and 11B, the SOI substrate SS is etched from the rear surface thereof so as to form each of the probes 20, 30, 40, 50A, and 50B into a cantilever shape. In this step, dry etching such as ICP-RIE is used. The support substrate SB of the SOI substrate SS is etched from the rear surface thereof. When the probes 20, 30, 40, 50A, and 50B are separated, the etching is stopped. By doing so, each of the probes 20, 30, 40, 50A, and 50B can be formed into a cantilever shape.

(5) (Side Wall Forming Step)

Figure 12A:
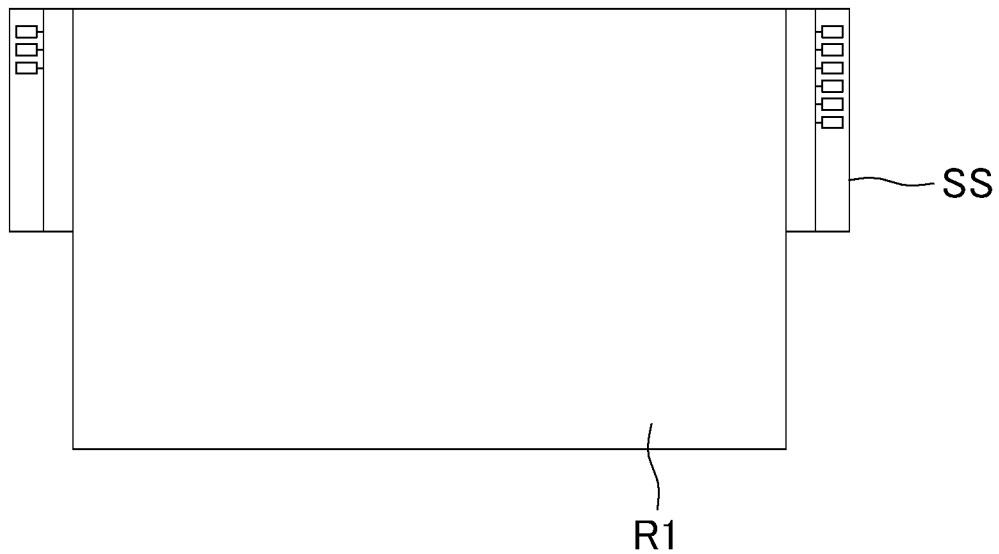
FIG. 12A is a plan view of the vascular sap measurement sensor in a side wall forming step (first half).
Figure 12B:
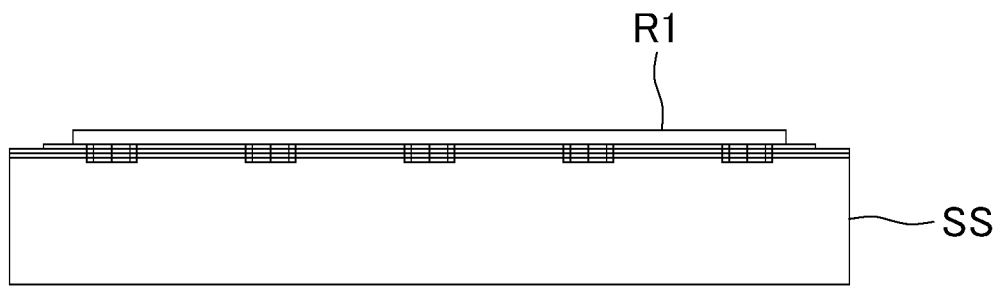
FIG. 12B is a front view of this vascular sap measurement sensor.

Next, as shown in FIGS. 12A and 12B, a sheet-like photoresist R1 is thermally fusion-bonded to a necessary region on the SOI substrate SS. The sheet-like photoresist R1 is not particularly limited, as long as it can be thermally fusion-bonded and has a certain degree of strength. A preferable material for the photoresist R1 is SU8.

Figure 13A:
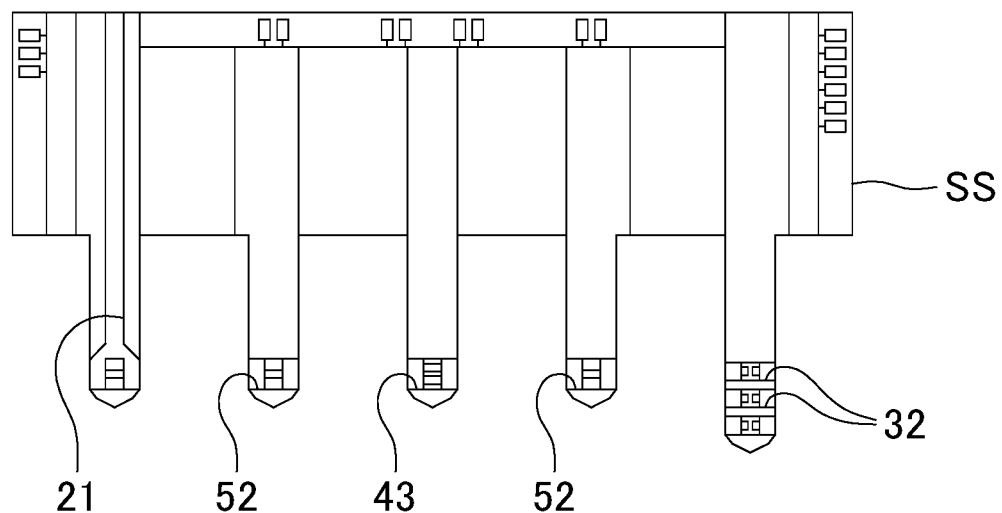
FIG. 13A is a plan view of the vascular sap measurement sensor in the side wall forming step (latter half).
Figure 13B:
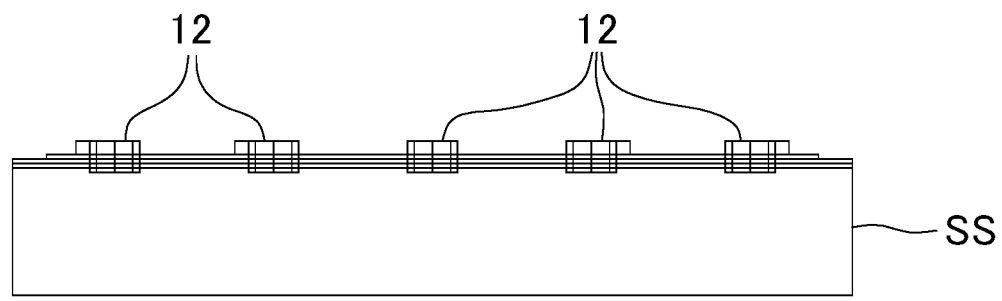
FIG. 13B is a front view of this vascular sap measurement sensor.

Next, as shown in FIGS. 13A and 13B, the photoresist R1 is subjected to exposure and development to remove an unnecessary part of the photoresist R1. More specifically, the removed unnecessary part includes parts protruding out from the probe shapes, and parts corresponding to the trapping flow channel 21, the electrode flow channel 32, and the temperature sensor flow channels 43 and 52.

By removing the parts of the photoresist R1 corresponding to the flow channels 21, 32, 43, and 52 of the corresponding types, the side walls 12 forming the flow channels 21, 32, 43, and 52 of the corresponding types can be formed on the SOI substrate SS.

In this way, the side walls 12 of the flow channels 21, 32, 43, and 52 of the corresponding types are formed using the photoresist R1, so that the resultant side walls 12 can be vertical to the SOI substrate SS. If crystalline anisotropic etching is used for forming the flow channels 21, 32, 43, and 52 directly in the SOI substrate SS, for example, the side walls 12 become tilted from the SOI substrate SS. Compared to this case, the cross-sectional areas of the flow channels 21, 32, 43, and 52 can be increased. This allows vascular sap to easily flow into the flow channels 21, 32, 43, and 52. Further, using the sheet-like photoresist R1 makes it possible to form the side walls 12 into a height of a sufficient degree, thereby allowing vascular sap to flow into the flow channels 21, 32, 43, and 52 easily.

(6) Hydrophilization Step

As described above, the side walls 12 are formed using the cured photoresist R1. The photoresist R1 is generally hydrophobic. Hence, using the photoresist R1 as it is makes it difficult for vascular sap to flow into the flow channels 21, 32, 43, and 52. In this regard, a process of giving hydrophilic property to the side walls 12 is performed. Giving hydrophilic property to the side walls 12 allows the vascular sap to flow into the flow channels 21, 32, 43, and 52 easily.

The hydrophilization process is performed by inserting the vascular sap measurement sensor 1 being formed into a plasma etching device or a reactive ion etching device, and performing surface treatment such as oxygen ashing using $O_2$ gas, for example. Etching proceeds with an oxygen radical ($O^*$) in plasma producing a chemical reaction expressed by the following chemical formula (1) on the surface of the sheet-like photoresist (main element composition is $C_xH_y$).

$$C_xH_y + O^* \rightarrow CO_2\uparrow + H_2O \quad (1)$$

In this process, the surface of the photoresist is altered (composition or structure on the surface is changed). Selecting an optimum oxygen ashing condition increases C—O bonds relative to C—C bonds or produces a new COO bond. When such a surface state is formed, a water molecule ($H_2O$) in the atmosphere and a bond on the surface of the photoresist react with each other to form C—OH or CO—OH and an OH group having polarity attracts the water molecule, thereby providing hydrophilic property (the property is changed from hydrophobic to hydrophilic). As an example, conditions for the reactive ion etching used in the hydrophilization process are as follows: an oxygen gas flow rate: 10 sccm, an oxygen gas pressure: 6.5 Pa, radiofrequency power: 100 W, and a period of the treatment: about five minutes.

(7) Ceiling Forming Step

Figure 14A:
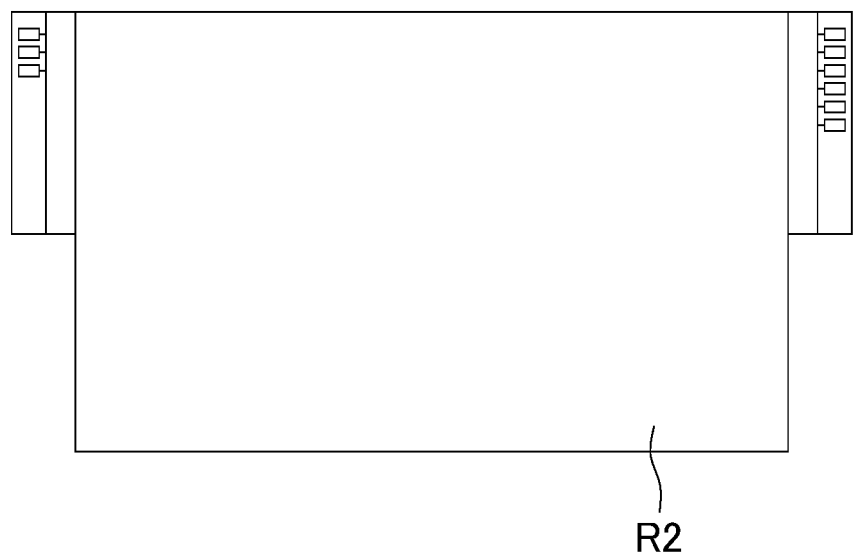
FIG. 14A is a plan view of the vascular sap measurement sensor in a ceiling forming step (first half).
Figure 14B:
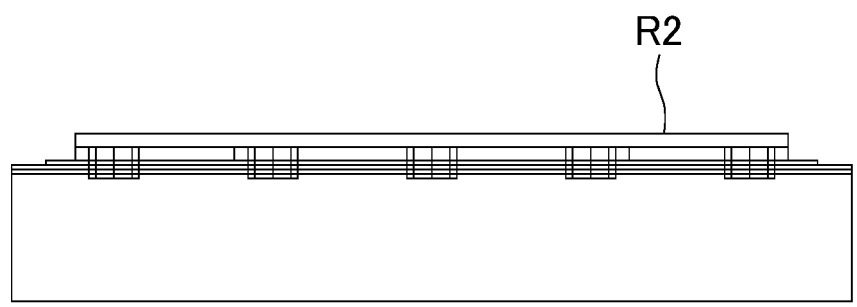
FIG. 14B is a front view of this vascular sap measurement sensor.

Next, as shown in FIGS. 14A and 14B, a different sheet-like photoresist R2 is thermally fusion-bonded on the cured photoresist R1. The photoresist R2 is thermally fusion-bonded to stretch across the upper ends of the side walls 12 forming the flow channels 21, 32, 43, and 52. The sheet-like photoresist R2 is not particularly limited, as long as it can be thermally fusion-bonded and has a certain degree of strength. A preferable material for the photoresist R2 is SU8.

Figure 15A:
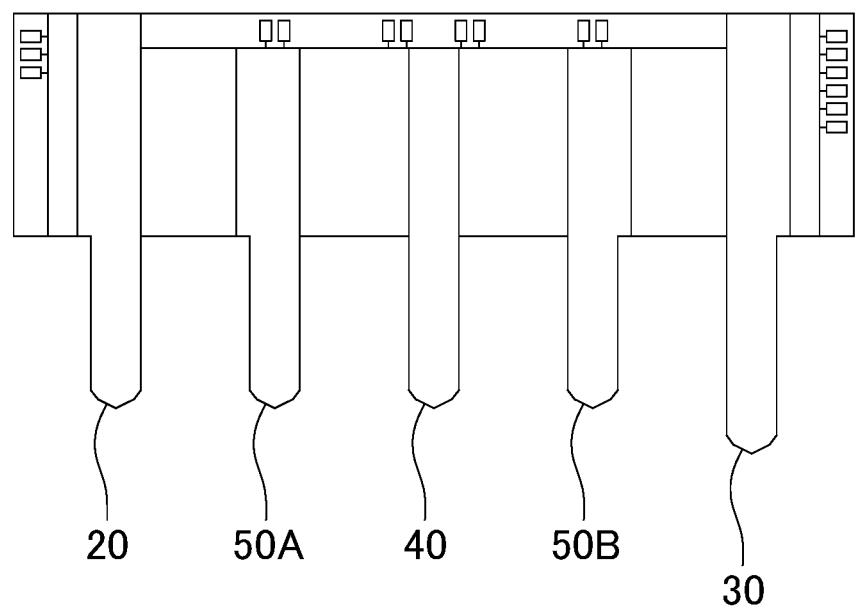
FIG. 15A is a plan view of the vascular sap measurement sensor in the ceiling forming step (latter half).
Figure 15B:
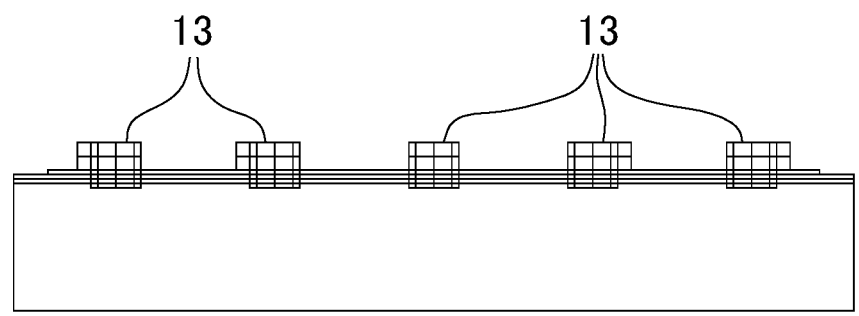
FIG. 15B is a front view of this vascular sap measurement sensor.

Next, as shown in FIGS. 15A and 15B, the photoresist R2 is subjected to exposure and development to remove an unnecessary part of the photoresist R2. The ceiling part 13 of each of the flow channels 21, 32, 43, and 52 can be formed using the photoresist R2.

In this way, the ceiling part 13 of each of the flow channels 21, 32, 43, and 52 is formed using the sheet-like photoresist R2, so that the flow channels 21, 32, 43, and 52 can be formed easily in corresponding ones of the probes 20, 30, 40, 50A, and 50B. Further, as the sheet-like photoresist R2 is used for forming the ceiling part 13 of the trapping flow channel 21, even the pH measurement element 26 sensitive to a surface state can still be formed easily in the trapping flow channel 21.

(8) Thermally Separating Step

Finally, as shown in FIGS. 1 and 2, the SOI substrate SS is cut in an area between a part supporting the heater-equipped temperature probe 40 and each part supporting each of the temperature probes 50A and 50B into a depth reaching the support substrate SB to form the groove 14. A method of forming the groove 14 is not particularly limited but it may be a method using a dicing saw, laser dicing, or etching, for example. The depth of the groove 14 is only required to be equal to or greater than the thickness of the active layer AL.

In the foregoing embodiment, the hydrophilization step is performed between the side wall forming step and the ceiling forming step. The hydrophilization step may be performed further after the ceiling forming step. Alternatively, the hydrophilization step may be performed only after the ceiling forming step. By doing so, not only the side wall 12 but also the ceiling part 13 can be given hydrophilic property. Specifically, the entire interior of each of the flow channels 21, 32, 43, and 52 can be given hydrophilic property. This allows vascular sap to flow into each of the flow channels 21, 32, 43, and 52 easily.

After the ceiling forming step, however, each of the flow channels 21, 32, 43, and 52 is surrounded by the bottom part 11, the side walls 12, and the ceiling part 13. Further, the inner wall of each of the flow channels 21, 32, 43, and 52 is continuous with the outside air only through an opening end of each of the flow channels 21, 32, 43, and 52 and there is difficulty for oxygen radicals to enter the flow channel sufficiently. For these reasons, the hydrophilization step takes a relatively long time. Before the ceiling forming step, the absence of the ceiling part 13 makes an entire upper part of each of the flow channels 21, 32, 43, and 52 continuous with the outside air. For this reason, performing the hydrophilization process before the ceiling forming step makes it possible to facilitate the process efficiently within a shorter time.

The oxide film is formed on the bottom part 11 of each of the flow channels 21, 32, 43, and 52. The oxide film generally has hydrophilic property. Giving hydrophilic property to the side walls 12 means that three surfaces of each of the flow channels 21, 32, 43, and 52 are given hydrophilic property. Thus, even if the ceiling part 13 is left as a hydrophobic part, vascular sap can still flow into the flow channels 21, 32, 43, and 52 sufficiently.

In the foregoing side wall forming step, the side walls 12 are formed using the photoresist R1. Alternatively, the side walls 12 may be formed using the SOI substrate SS by removing parts of the SOI substrate SS corresponding to the flow channels 21, 32, 43, and 52 by etching.

In this case, the bottom part 11 and the side walls 12 of each of the flow channels 21, 32, 43, and 52 are formed integrally by the use of the SOI substrate SS to allow increase in the strengths of the probes 20, 30, 40, 50A, and 50B. Further, by the presence of hydrophilic property inherent in the bottom part 11 and the side walls 12, the hydrophilization step may be omitted.

Second Embodiment

A vascular sap measurement sensor 2 according to a second embodiment of this invention will be described next. A member comparable to that of the vascular sap measurement sensor 1 according to the first embodiment will be identified by the same sign and description of such a member will be omitted.

Figure 16:
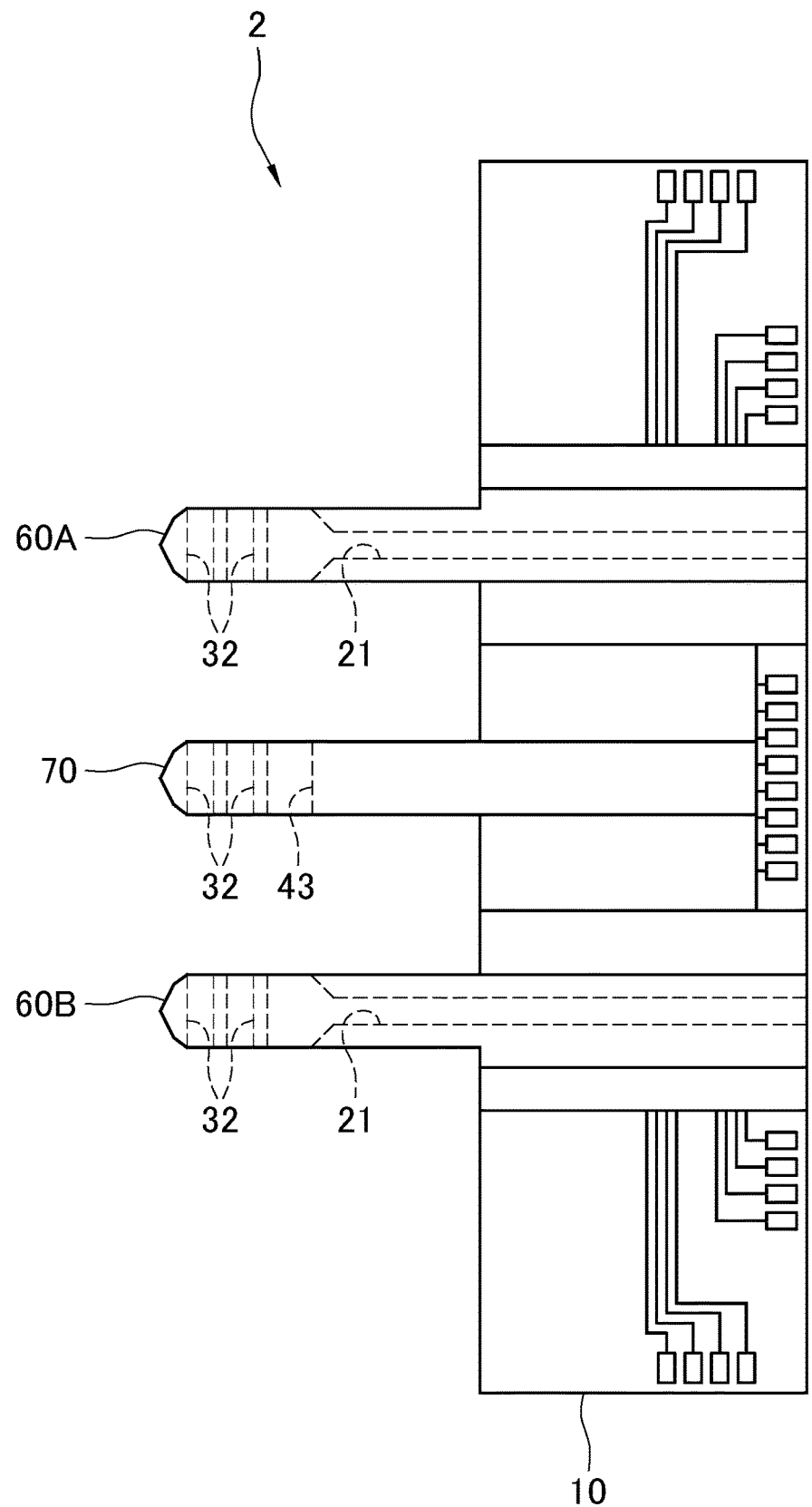
FIG. 16 is a plan view of a vascular sap measurement sensor according to a second embodiment.

As shown in FIG. 16, the vascular sap measurement sensor 2 includes the support 10, lateral probes 60A and 60B in a pair, and one center probe 70.

While all the probes 60A, 60B, and 70 are aligned parallel to each other in the same horizontal plane, the base end of each of these probes 60A, 60B, and 70 is supported on the support 10. The lateral probes 60A and 60B in a pair are provided at positions between which the center probe 70 is located. The vascular sap measurement sensor 2 is installed on a plant by sticking the probes 60A, 60B, and 70 into a stem of the plant, for example.

(Lateral Probe)

Each of the lateral probes 60A and 60B is a probe as an integration of the trapping probe 20, the electrical resistance probe 30, and the temperature probe 50A or 50B of the first embodiment. More specifically, each of the lateral probes 60A and 60B includes the trapping flow channel 21, the electrical resistance measurement electrode 31, and the temperature sensor 51.

Figure 18:
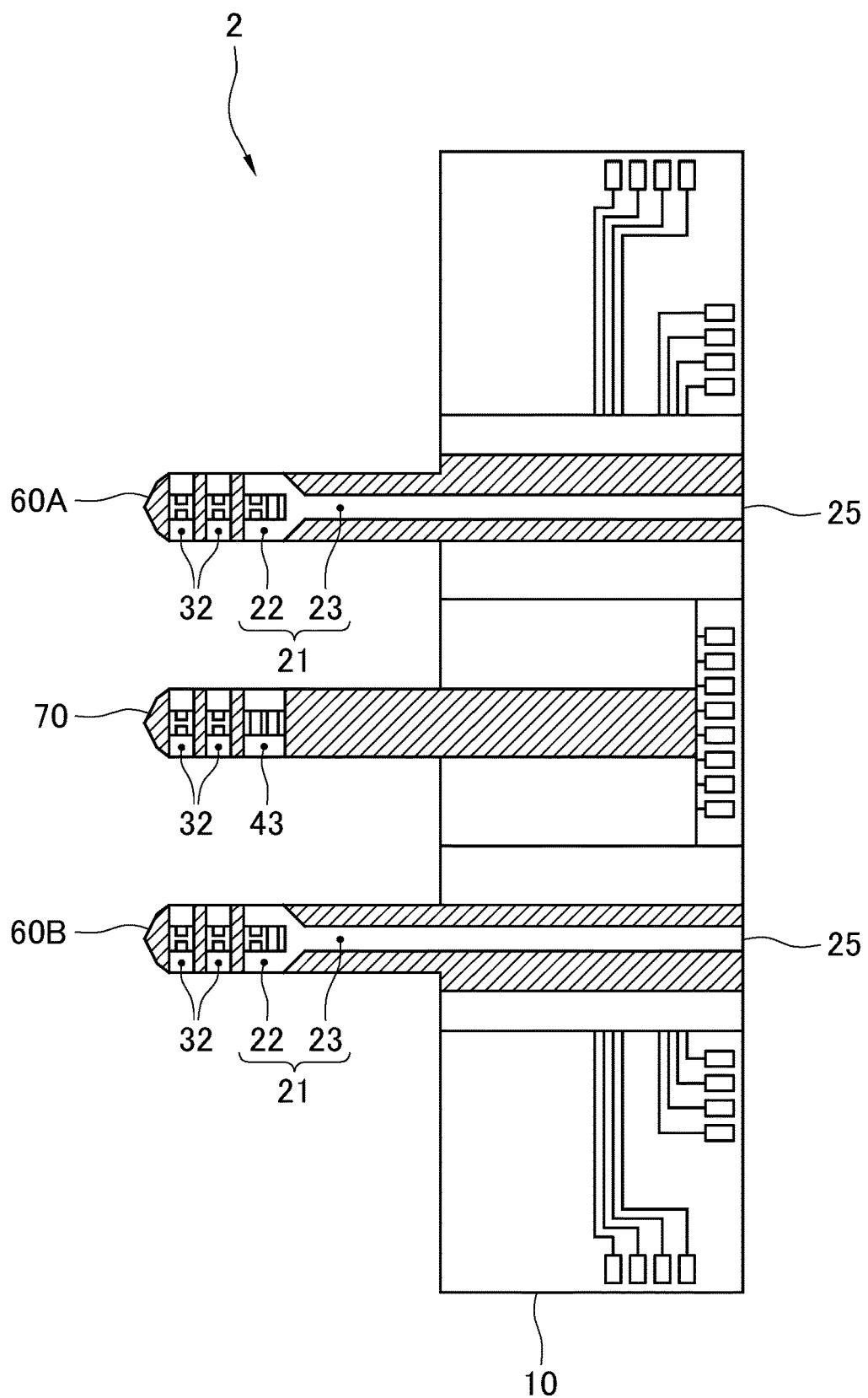
FIG. 18 is a sectional view taken along an arrowed line XVIII-XVIII of FIG. 17.
Figure 19A:
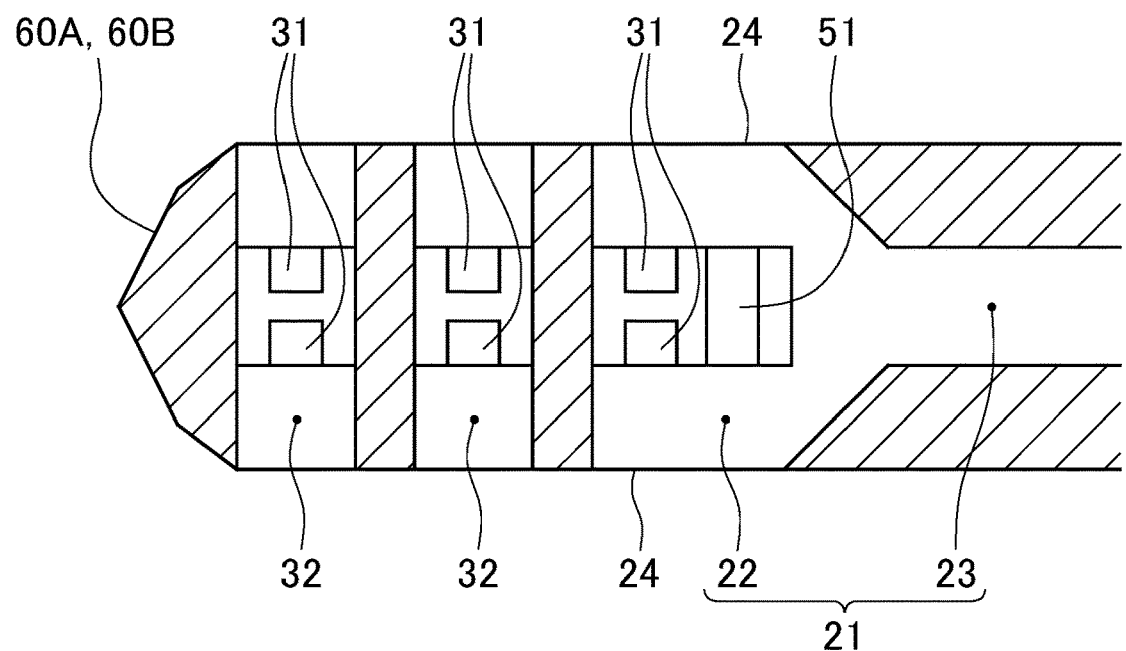
FIG. 19A is an enlarged transverse sectional view of a tip portion of a lateral probe.

As shown in FIGS. 18 and 19A, the trapping flow channel 21 is formed in each of the lateral probes 60A and 60B. The trapping flow channel 21 as a whole is substantially T-shaped, and includes the first flow channel 22 and the second flow channel 23. The trapping flow channel 21 has the two inlet openings 24 and 24. One of the inlet openings 24 is arranged on one side surface of each of the lateral probes 60A and 60B. The other inlet opening 24 is arranged on the other side surface of each of the lateral probes 60A and 60B. The first flow channel 22 connects the two inlet openings 24 and 24 and extends in the width direction of each of the lateral probes 60A and 60B. The second flow channel 23 has one end connected to the first flow channel 22 and extends in the axis direction of each of the lateral probes 60A and 60B. The pH measurement element 26 may be provided in the trapping flow channel 21.

Two electrode flow channels 32 are formed in each of the lateral probes 60A and 60B and at positions closer to the tip than the trapping flow channel 21. Each electrode flow channel 32 extends in the width direction of each of the lateral probes 60A and 60B and has openings arranged on opposite side surfaces of each of the lateral probes 60A and 60B. Thus, by sticking each of the lateral probes 60A and 60B into a stem of a plant, for example, vascular sap is caused to flow into the electrode flow channel 32.

The two electrode flow channels 32 are aligned in the axis direction of each of the lateral probes 60A and 60B. The electrical resistance measurement electrodes 31 in a pair are provided in each of the two electrode flow channels 32. In this way, the electrical resistance measurement electrodes 31 are aligned in units of pairs in the axis direction of each of the lateral probes 60A and 60B.

The electrical resistance measurement electrodes 31 in a pair are further provided in the first flow channel 22 of the trapping flow channel 21. In this way, the first flow channel 22 forms a part of the trapping flow channel 21 and further functions as the electrode flow channel 32.

The temperature sensor 51 is provided in the first flow channel 22 of the trapping flow channel 21. In this way, the first flow channel 22 forms a part of the trapping flow channel 21 and further functions as the temperature sensor flow channel 52.

(Center Probe)

The center probe 70 is a probe as an integration of the electrical resistance probe 30 and the heater-equipped temperature probe 40 of the first embodiment. More specifically, the center probe 70 includes the electrical resistance measurement electrode 31, the temperature sensor 41, and the heater 42.

Figure 19B:
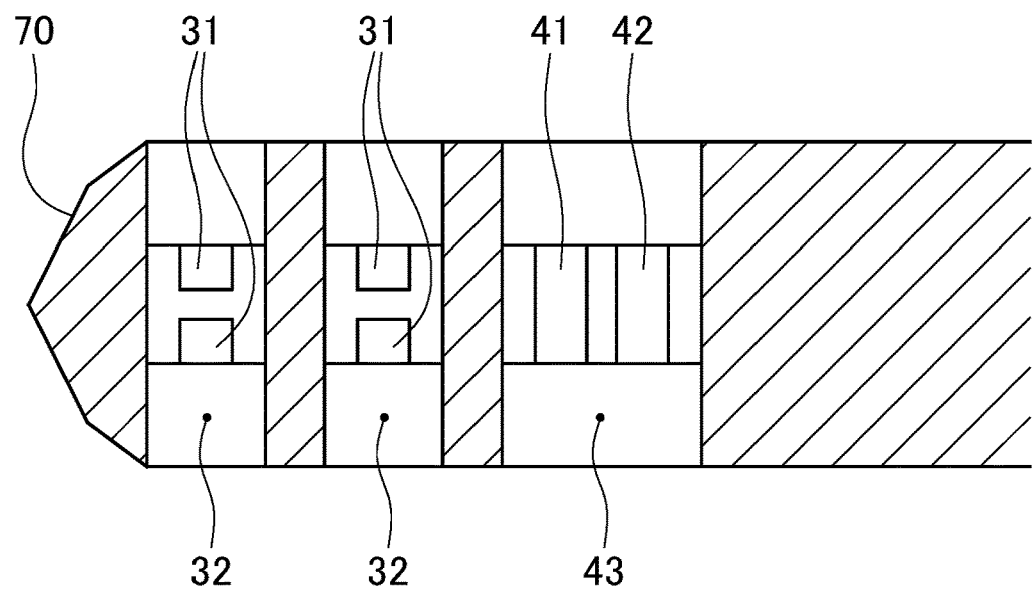
FIG. 19B is an enlarged transverse sectional view of a tip portion of a center probe.

As shown in FIGS. 18 and 19B, the center probe 70 has a tip portion in which two electrode flow channels 32 are formed. Each electrode flow channel 32 includes the electrical resistance measurement electrodes 31 in a pair provided therein.

The temperature sensor flow channel 43 is formed in the tip portion of the center probe 70. The two electrode flow channels 32 are arranged closer to the tip than the temperature sensor flow channel 43. The temperature sensor 41 and the heater 42 are provided in the temperature sensor flow channel 43.

Figure 17:
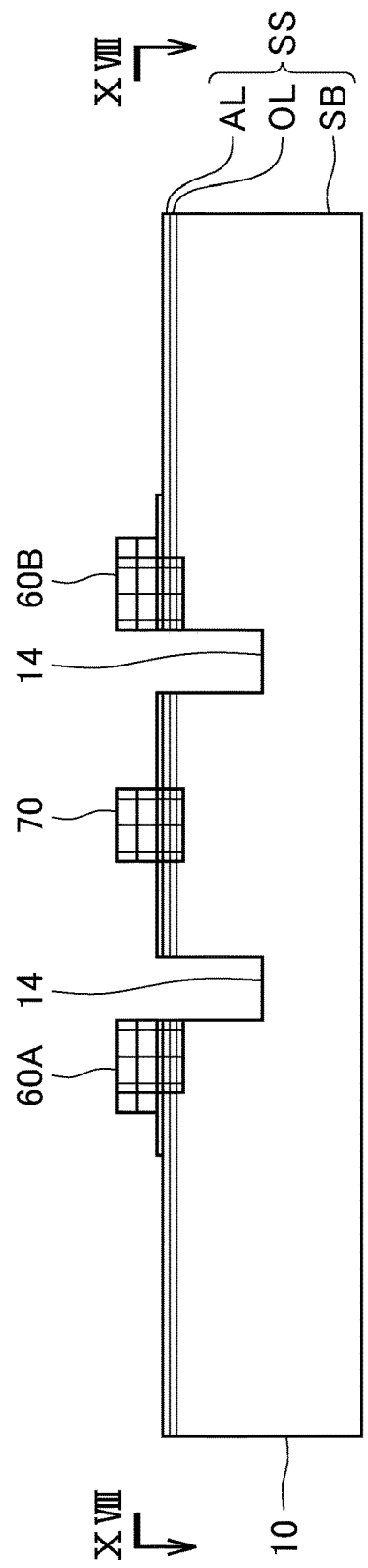
FIG. 17 is a front view of the vascular sap measurement sensor of FIG. 16.

As shown in FIG. 17, the groove 14 is formed between a part of the support 10 supporting the center probe 70 and each part of the support 10 supporting each of the lateral probes 60A and 60B. This makes it unlikely that heat of the heater 42 of the center probe 70 will be transmitted via the support 10 to each of the lateral probes 60A and 60B.

(Method of Use)

A method of using the vascular sap measurement sensor 2 will be described next.

Figure 20:
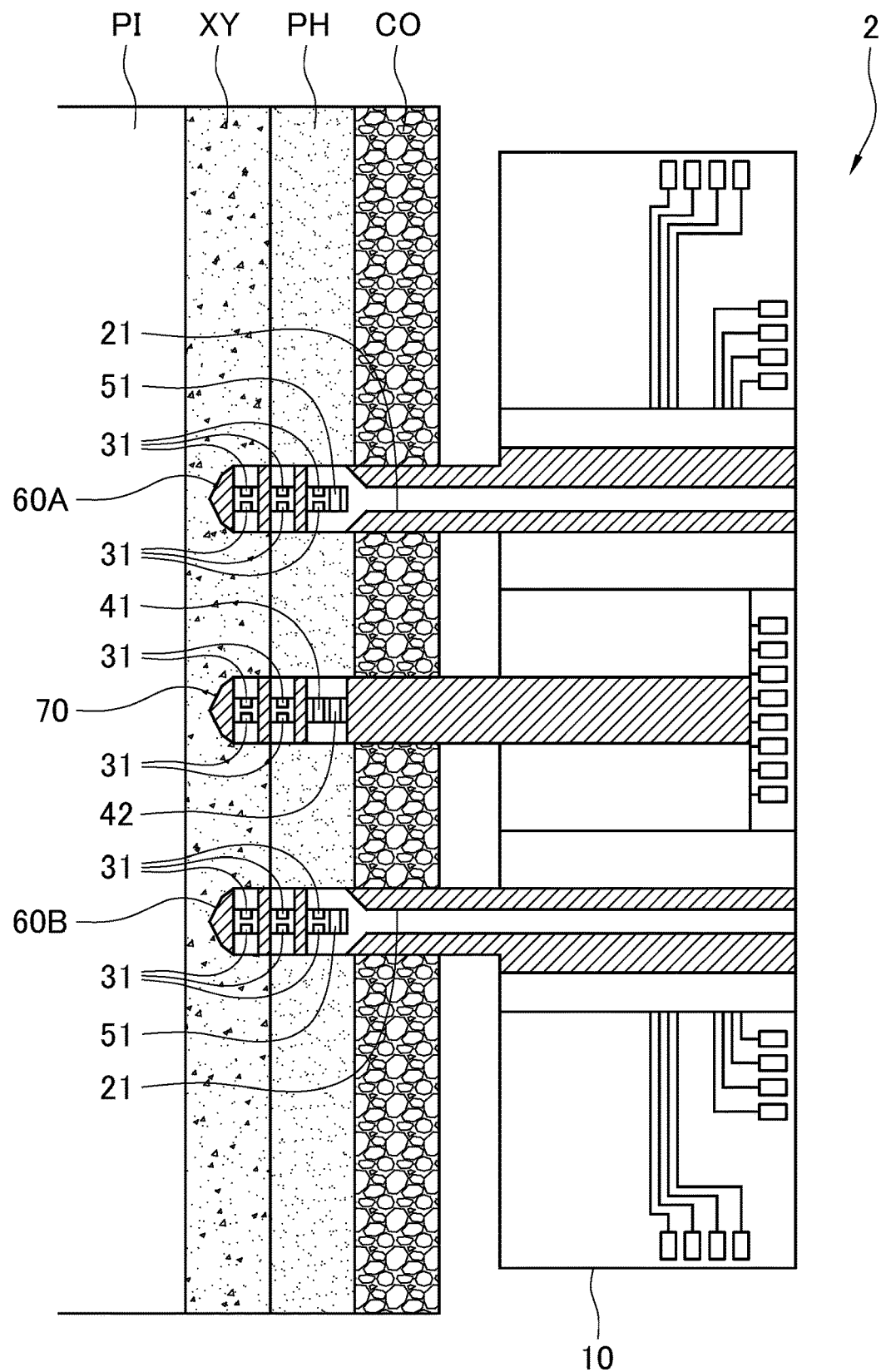
FIG. 20 explains a condition of use of the vascular sap measurement sensor of FIG. 16.

As shown in FIG. 20, the vascular sap measurement sensor 2 is attached by sticking all the probes 60A, 60B, and 70 of the vascular sap measurement sensor 2 into a fine point of the plant. At this time, the probes 60A, 60B, and 70 are arranged along the xylem XY and the phloem PH.

Each of the probes 60A, 60B, and 70 includes the electrical resistance measurement electrode 31 and has a function of detecting the position of the xylem XY. Depths of sticking of the probes 60A, 60B, and 70 can be adjusted based on the detected position of the xylem XY.

Vascular sap can be trapped in the trapping flow channel 21 provided at each of the lateral probes 60A and 60B. Based on temperatures measured by the temperature sensors 41 and 51 after starting the heater 42 provided at the center probe 70, the direction and the flow rate of a vascular sap flow can be determined.

The second embodiment includes the probes 60A, 60B, and 70 of a reduced number. This can reduce the size of the vascular sap measurement sensor 2. The small number of the probes 60A, 60B, and 70 can further alleviate damage (injury) to a plant.

The trapping probe 20, the electrical resistance probe 30, the heater-equipped temperature probe 40, and the temperature probes 50A and 50B of the first embodiment can be combined and integrated in any way.

Other Embodiment

Figure 21:
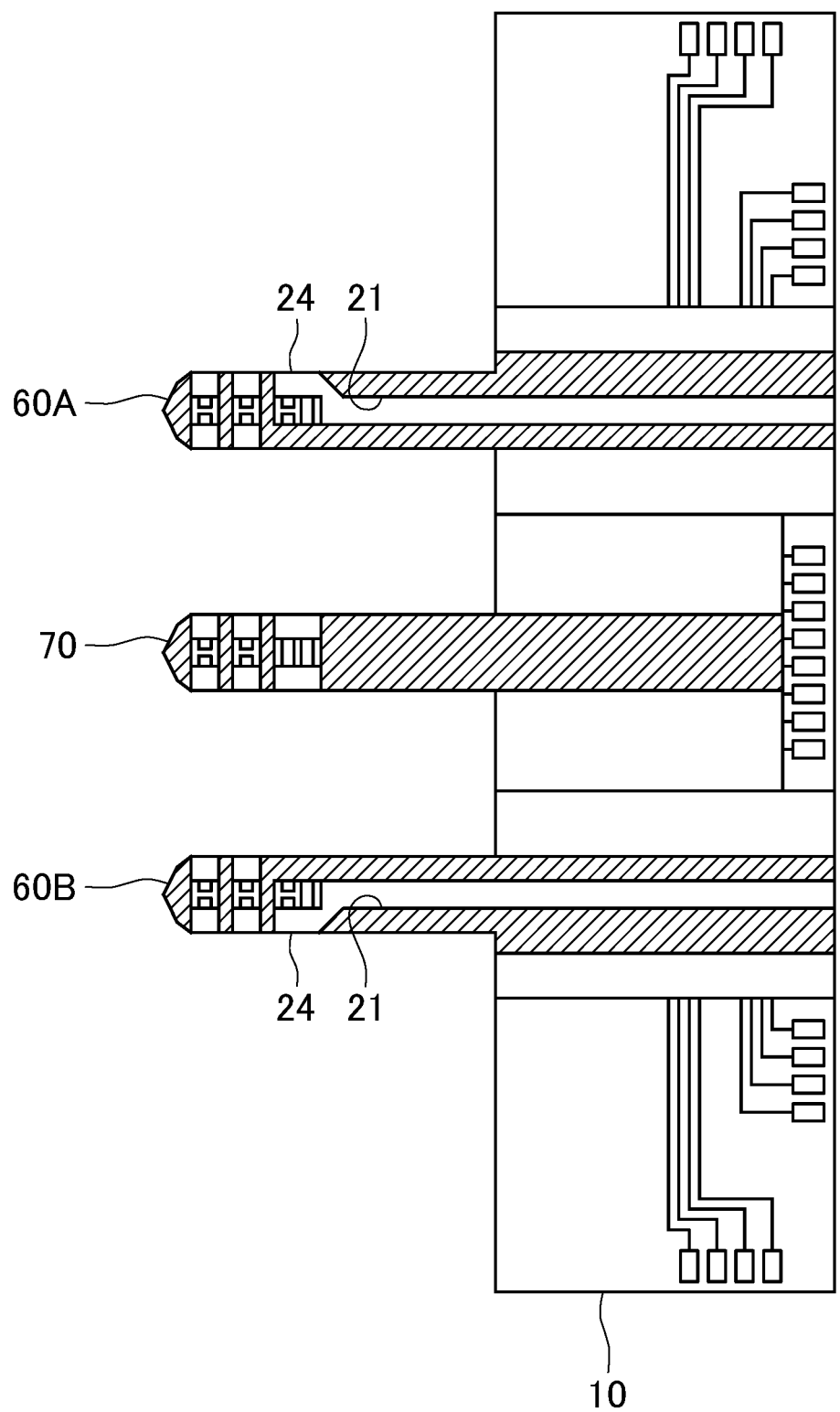
FIG. 21 is a transverse sectional view of a vascular sap measurement sensor according to a different embodiment.

In the foregoing embodiments, the number of the inlet openings 24 at the trapping flow channel 21 is two. Alternatively, one inlet opening 24 may be provided. As shown in FIG. 21, for example, the trapping flow channel 21 formed at each of the lateral probes 60A and 60B is configured to be substantially L-shaped as a whole and to have only one inlet opening 24. The inlet opening 24 is formed on one side surface of each of the lateral probes 60A and 60B.

Arranging the inlet opening 24 of the trapping flow channel 21 on only one side of each of the lateral probes 60A and 60B makes it possible to reduce the occurrence of outgoing flow of vascular sap having flowed into the trapping flow channel 21 through the inlet opening 24, thereby allowing efficient trapping of the vascular sap.

In this case, the inlet opening 24 of the trapping flow channel 21 formed at one lateral probe 60A and the inlet opening 24 of the trapping flow channel 21 formed at the other lateral probe 60B are preferably pointed in opposite directions, and each inlet opening 24 is preferably pointed laterally. This makes it possible to trap vascular sap at either of the lateral probes 60A and 60B independently of the direction of a vascular sap flow. As a result, the lateral probes 60A and 60B can be stuck into a plant without the need of caring for the direction of the sticking.

Figure 22:
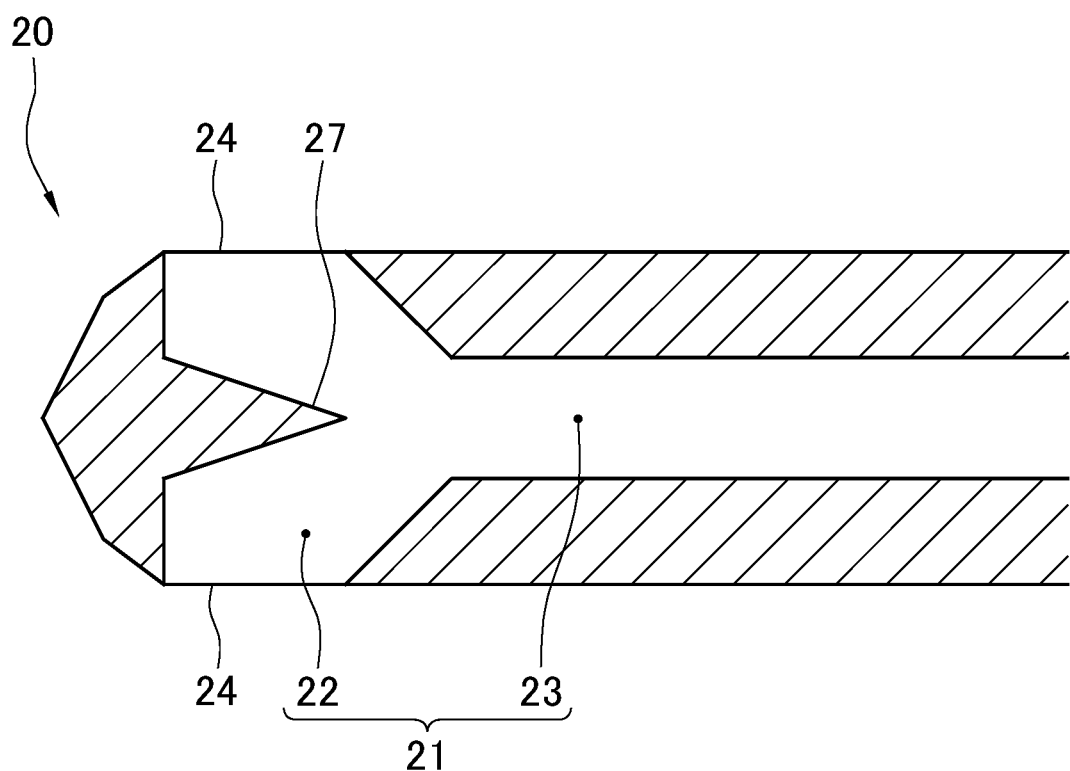
FIG. 22 is an enlarged transverse sectional view of a tip portion of a trapping probe according to a still different embodiment.

As shown in FIG. 22, in the configuration where the trapping flow channel 21 has two inlet openings 24, a guide wall 27 may be provided in the first flow channel 22 connecting the two inlet openings 24. By the presence of the guide wall 27, vascular sap having flowed into the first flow channel 22 through the inlet opening 24 can be guided to the second flow channel 23. This can make it unlikely that the vascular sap having flowed into the trapping flow channel 21 through one of the inlet openings 24 will flow out through the other inlet opening 24, thereby allowing efficient trapping of the vascular sap.

Figure 23:
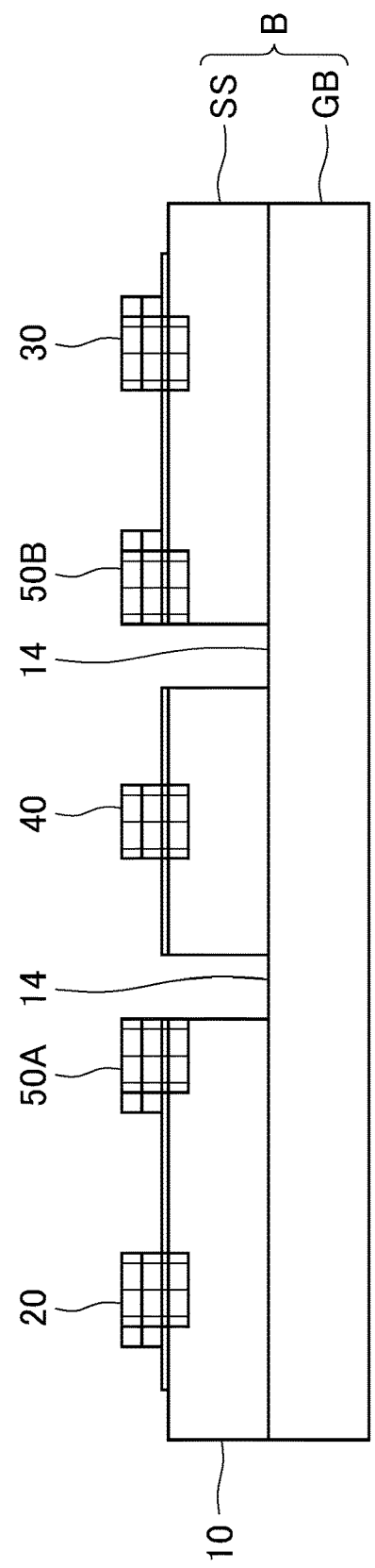
FIG. 23 is a front view of a vascular sap measurement sensor according to a still different embodiment.

As shown in FIG. 23, the support 10 may be formed of a substrate B as a stack of an insulating substrate GB and the semiconductor substrate SS. Each of the probes 20, 30, 40, 50A, and 50B is formed at the semiconductor substrate SS. A substrate made of an insulating material such as a glass substrate is used as the insulating substrate GB.

The groove 14 is formed between a part of the support 10 supporting the heater-equipped temperature probe 40 and each part of the support 10 supporting each of the temperature probes 50A and 50B. The groove 14 is formed by removing the semiconductor substrate SS. A method of forming the groove 14 is not particularly limited but it may be a method using a dicing saw, laser dicing, or etching, for example.

By the presence of the groove 14 formed between the heater-equipped temperature probe 40 and each of the temperature probes 50A and 50B, the heater-equipped temperature probe 40 and each of the temperature probes 50A and 50B become connected to each other via the insulating substrate GB having high heat insulating property. Specifically, the heater-equipped temperature probe 40 and each of the temperature probes 50A and 50B are thermally separated from each other. This makes it unlikely that heat of the heater 42 of the heater-equipped temperature probe 40 will be transmitted via the support 10 to each of the temperature probes 50A and 50B. As a result, the temperature of vascular sap can be measured with high accuracy using the temperature sensor 51 of each of the temperature probes 50A and 50B, making it possible to determine the flow speed of the vascular sap with high accuracy and determine a flow rate from the determined flow speed with high accuracy.

A vascular sap measurement sensor having the foregoing configuration can be manufactured by forming the sensor unit on the front surface of the semiconductor substrate SS, then adhesively attaching the insulating substrate GB to the rear surface of the semiconductor substrate SS, and then forming the probes.

The vascular sap measurement sensor is not required to include all of the trapping probe 20, the electrical resistance probe 30, the heater-equipped temperature probe 40, and the temperature probes 50A and 50B. The presence of the trapping probe 20 in the vascular sap measurement sensor is sufficient for trapping vascular sap. The vascular sap measurement sensor may be configured to include only the trapping probe 20, or include only the trapping probe 20 and the electrical resistance probe 30.

The presence of the heater-equipped temperature probe 40 and the temperature probes 50A and 50B in the vascular sap measurement sensor is sufficient for measuring the direction and the flow rate of a vascular sap flow. The vascular sap measurement sensor may be configured to include only the heater-equipped temperature probe 40 and the temperature probes 50A and 50B, or include only the heater-equipped temperature probe 40, the temperature probes 50A and 50B, and the electrical resistance probe 30.

The vascular sap measurement sensor may include one temperature probe 50A or 50B. In this case, the heater-equipped temperature probe 40 is arranged on a downstream side of vascular sap and the temperature probe 50A is arranged on an upstream side of the vascular sap. This arrangement allows measurement of the flow rate of the vascular sap.

REFERENCE SIGNS LIST 1, 2 Vascular sap measurement sensor
10 Support
20 Trapping probe
21 Trapping flow channel
24 Inlet opening
26 pH measurement element
30 Electrical resistance probe
31 Electrical resistance measurement electrode
32 Electrode flow channel
40 Heater-equipped temperature probe
41 Temperature sensor
42 Heater
43 Temperature sensor flow channel
50A, 50B Temperature probe
51 Temperature sensor
52 Temperature sensor flow channel
60A, 60B Lateral probe
70 Center probe

The invention claimed is:
1. A vascular sap measurement sensor, comprising:
a trapping probe for trapping vascular sap; and
a support that supports the trapping probe, wherein
a trapping flow channel that receives incoming flow of the vascular sap is formed in the trapping probe, and
the trapping flow channel has an inlet opening arranged on a side surface of the trapping probe.

2. The vascular sap measurement sensor according to claim 1, wherein
the trapping flow channel has two inlet openings, one of the inlet openings is arranged on one of side surfaces of the trapping probe, and the other inlet opening is formed on the other side surface of the trapping probe.

3. The vascular sap measurement sensor according to claim 2, wherein
the trapping flow channel includes:
a first flow channel connecting the two inlet openings and extending in the width direction of the trapping probe; and
a second flow channel having one end connected to the first flow channel and extending in the axis direction of the trapping probe, and
a guide wall is provided in the first flow channel, the guide wall guiding the vascular sap having flowed into the first flow channel through the inlet opening to the second flow channel.

4. The vascular sap measurement sensor according to claim 1, wherein
the trapping flow channel has one inlet opening, and the inlet opening is formed on one side surface of the trapping probe.

5. The vascular sap measurement sensor according to claim 1, wherein
a pH measurement element is provided in the trapping flow channel.

6. The vascular sap measurement sensor according to claim 1, comprising:
an electrical resistance probe with an electrical resistance measurement electrode, wherein
the electrical resistance probe is supported on the support,
an electrode flow channel that receives incoming flow of the vascular sap is formed in the electrical resistance probe,
the electrode flow channel extends in the width direction of the electrical resistance probe,
the electrode flow channel has an opening arranged on a side surface of the electrical resistance probe, and
the electrical resistance measurement electrode is provided in the electrode flow channel.

7. The vascular sap measurement sensor according to claim 6, wherein
the electrical resistance probe includes a plurality of the electrode flow channels,
the electrode flow channels are aligned in the axis direction of the electrical resistance probe, and
each of the electrode flow channels is provided with the electrical resistance measurement electrode.

8. The vascular sap measurement sensor according to claim 1, comprising:
a heater-equipped temperature probe with a temperature sensor and a heater; and
a temperature probe with a temperature sensor, wherein
the heater-equipped temperature probe and the temperature probe are supported on the support.

9. The vascular sap measurement sensor according to claim 8, wherein
a temperature sensor flow channel that receives incoming flow of the vascular sap is formed in the heater-equipped temperature probe,
the temperature sensor flow channel extends in the width direction of the heater-equipped temperature probe,
the temperature sensor flow channel has an opening arranged on a side surface of the heater-equipped temperature probe, and
the temperature sensor is provided in the temperature sensor flow channel.

10. The vascular sap measurement sensor according to claim 8, wherein
a temperature sensor flow channel that receives incoming flow of the vascular sap is formed in the temperature probe,
the temperature sensor flow channel extends in the width direction of the temperature probe,
the temperature sensor flow channel has an opening arranged on a side surface of the temperature probe, and
the temperature sensor is provided in the temperature sensor flow channel.

11. The vascular sap measurement sensor according to claim 8, wherein
the support is formed of a stack of an insulating substrate and a semiconductor substrate,
the heater-equipped temperature probe and the temperature probe are formed at the semiconductor substrate, and
the support has a groove where the semiconductor substrate is removed, the groove being formed between a part of the support supporting the heater-equipped temperature probe and a part of the support supporting the temperature probe.

12. A vascular sap measurement sensor, comprising:
a heater-equipped temperature probe with a temperature sensor and a heater;
a temperature probe with a temperature sensor; and
a support that supports the heater-equipped temperature probe and the temperature probe, wherein
a temperature sensor flow channel that receives incoming flow of vascular sap is formed in the heater-equipped temperature probe,
the temperature sensor flow channel extends in the width direction of the heater-equipped temperature probe,
the temperature sensor flow channel has an opening arranged on a side surface of the heater-equipped temperature probe, and
the temperature sensor is provided in the temperature sensor flow channel.

13. The vascular sap measurement sensor according to claim 12, wherein
a temperature sensor flow channel that receives incoming flow of the vascular sap is formed in the temperature probe,
the temperature sensor flow channel extends in the width direction of the temperature probe,
the temperature sensor flow channel has an opening arranged on a side surface of the temperature probe, and
the temperature sensor is provided in the temperature sensor flow channel.

14. A vascular sap measurement sensor, comprising:
a heater-equipped temperature probe with a temperature sensor and a heater;
a temperature probe with a temperature sensor; and
a support that supports the heater-equipped temperature probe and the temperature probe, wherein
a temperature sensor flow channel that receives incoming flow of vascular sap is formed in the temperature probe,
the temperature sensor flow channel extends in the width direction of the temperature probe,
the temperature sensor flow channel has an opening arranged on a side surface of the temperature probe, and
the temperature sensor is provided in the temperature sensor flow channel.

15. The vascular sap measurement sensor according to claim 12, wherein
the support is formed of a stack of an insulating substrate and a semiconductor substrate,
the heater-equipped temperature probe and the temperature probe are formed at the semiconductor substrate, and
the support has a groove where the semiconductor substrate is removed, the groove being formed between a part of the support supporting the heater-equipped temperature probe and a part of the support supporting the temperature probe.

16. The vascular sap measurement sensor according to claim 12, comprising:
an electrical resistance probe with an electrical resistance measurement electrode, wherein
the electrical resistance probe is supported on the support,
an electrode flow channel that receives incoming flow of the vascular sap is formed in the electrical resistance probe,
the electrode flow channel extends in the width direction of the electrical resistance probe,
the electrode flow channel has an opening arranged on a side surface of the electrical resistance probe, and
the electrical resistance measurement electrode is provided in the electrode flow channel.

17. The vascular sap measurement sensor according to claim 16, wherein
the electrical resistance probe includes a plurality of the electrode flow channels,
the electrode flow channels are aligned in the axis direction of the electrical resistance probe, and
each of the electrode flow channels is provided with the electrical resistance measurement electrode.

18. A method of manufacturing a vascular sap measurement sensor including a trapping probe with a trapping flow channel that receives incoming flow of vascular sap, the method comprising:
a side wall forming step of forming side walls of the trapping flow channel on a semiconductor substrate, the trapping flow channel having an inlet opening arranged on a side surface of the trapping probe; and
a ceiling forming step of forming a ceiling part of the trapping flow channel by thermally fusion-bonding a sheet-like photoresist to stretch the photoresist across the upper ends of the side walls and removing an unnecessary part of the photoresist.

19. The method of manufacturing the vascular sap measurement sensor according to claim 18, wherein
in the side wall forming step, the side walls are formed by thermally fusion-bonding a sheet-like photoresist and removing a part of the photoresist corresponding to the trapping flow channel.

20. The method of manufacturing the vascular sap measurement sensor according to claim 18, wherein
in the side wall forming step, the side walls are formed by removing a part of the semiconductor substrate corresponding to the trapping flow channel.

21. The method of manufacturing the vascular sap measurement sensor according to claim 18, comprising:
a hydrophilization step of giving hydrophilic property to the side walls performed after the side wall forming step.

22. The method of manufacturing the vascular sap measurement sensor according to claim 18, comprising:
a hydrophilization step of giving hydrophilic property to an interior of the trapping flow channel performed after the ceiling forming step.

23. A method of manufacturing a vascular sap measurement sensor including a heater-equipped temperature probe with a temperature sensor flow channel that receives incoming flow of vascular sap, the method comprising:
a side wall forming step of forming side walls of the temperature sensor flow channel on a semiconductor substrate, the temperature sensor flow channel having an inlet opening arranged on a side surface of the heater-equipped temperature probe; and
a ceiling forming step of forming a ceiling part of the temperature sensor flow channel by thermally fusion-bonding a sheet-like photoresist to stretch the photoresist across the upper ends of the side walls and removing an unnecessary part of the photoresist.

24. The method of manufacturing the vascular sap measurement sensor according to claim 23, wherein
in the side wall forming step, the side walls are formed by thermally fusion-bonding a sheet-like photoresist and removing a part of the photoresist corresponding to the temperature sensor flow channel.

25. The method of manufacturing the vascular sap measurement sensor according to claim 23, wherein
in the side wall forming step, the side walls are formed by removing a part of the semiconductor substrate corresponding to the temperature sensor flow channel.

26. The method of manufacturing the vascular sap measurement sensor according to claim 23, comprising:
a hydrophilization step of giving hydrophilic property to the side walls performed after the side wall forming step.

27. The method of manufacturing the vascular sap measurement sensor according to claim 23, comprising:
a hydrophilization step of giving hydrophilic property to an interior of the temperature sensor flow channel performed after the ceiling forming step.

28. A method of manufacturing a vascular sap measurement sensor including a temperature probe with a temperature sensor flow channel that receives incoming flow of vascular sap, the method comprising:
a side wall forming step of forming side walls of the temperature sensor flow channel on a semiconductor substrate, the temperature sensor flow channel having an inlet opening arranged on a side surface of the temperature probe; and
a ceiling forming step of forming a ceiling part of the temperature sensor flow channel by thermally fusion-bonding a sheet-like photoresist to stretch the photoresist across the upper ends of the side walls and removing an unnecessary part of the photoresist.

29. The method of manufacturing the vascular sap measurement sensor according to claim 28, wherein
in the side wall forming step, the side walls are formed by thermally fusion-bonding a sheet-like photoresist and removing a part of the photoresist corresponding to the temperature sensor flow channel.

30. The method of manufacturing the vascular sap measurement sensor according to claim 28, wherein
in the side wall forming step, the side walls are formed by removing a part of the semiconductor substrate corresponding to the temperature sensor flow channel.

31. The method of manufacturing the vascular sap measurement sensor according to claim 28, comprising:
a hydrophilization step of giving hydrophilic property to the side walls performed after the side wall forming step.

32. The method of manufacturing the vascular sap measurement sensor according to claim 28, comprising:
a hydrophilization step of giving hydrophilic property to an interior of the temperature sensor flow channel performed after the ceiling forming step.

33. The vascular sap measurement sensor according to claim 14, wherein
the support is formed of a stack of an insulating substrate and a semiconductor substrate, the heater-equipped temperature probe and the temperature probe are formed at the semiconductor substrate, and
the support has a groove where the semiconductor substrate is removed, the groove being formed between a part of the support supporting the heater-equipped temperature probe and a part of the support supporting the temperature probe.

34. The vascular sap measurement sensor according to claim 14, comprising:
an electrical resistance probe with an electrical resistance measurement electrode, wherein
the electrical resistance probe is supported on the support,
an electrode flow channel that receives incoming flow of the vascular sap is formed in the electrical resistance probe,
the electrode flow channel extends in the width direction of the electrical resistance probe,
the electrode flow channel has an opening arranged on a side surface of the electrical resistance probe, and
the electrical resistance measurement electrode is provided in the electrode flow channel.

* * * * *